(12) United States Patent
Mosher et al.

(10) Patent No.: US 9,399,067 B2
(45) Date of Patent: *Jul. 26, 2016

(54) PHARMACEUTICAL COMPOSITIONS COMPRISING PRASUGREL AND CYCLODEXTRIN DERIVATIVES AND METHODS OF MAKING AND USING THE SAME

(71) Applicant: Cydex Pharmaceuticals, Inc., Lenexa, KS (US)

(72) Inventors: Gerold L. Mosher, Kansas City, MO (US); Stephen G. Machatha, Waltham, MA (US); Daniel J. Cushing, Phoenixville, PA (US)

(73) Assignee: CyDex Pharmaceuticals, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/485,195

(22) Filed: Sep. 12, 2014

(65) Prior Publication Data

US 2015/0005341 A1 Jan. 1, 2015

Related U.S. Application Data

(63) Continuation of application No. 13/542,253, filed on Jul. 5, 2012, now Pat. No. 8,835,407, which is a continuation of application No. 12/779,850, filed on May 13, 2010, now Pat. No. 8,236,782.

(60) Provisional application No. 61/177,718, filed on May 13, 2009.

(51) Int. Cl.
| | |
|---|---|
| *A61K 47/40* | (2006.01) |
| *A61K 31/4365* | (2006.01) |
| *A61K 9/00* | (2006.01) |
| *A61K 47/48* | (2006.01) |
| *B82Y 5/00* | (2011.01) |
| *C08B 37/16* | (2006.01) |

(52) U.S. Cl.
CPC ............... *A61K 47/40* (2013.01); *A61K 9/0019* (2013.01); *A61K 31/4365* (2013.01); *A61K 47/48969* (2013.01); *B82Y 5/00* (2013.01); *C08B 37/0012* (2013.01)

(58) Field of Classification Search
None
See application file for complete search history.

(56) References Cited

U.S. PATENT DOCUMENTS

| | | |
|---|---|---|
| 3,426,011 A | 2/1969 | Parmerter et al. |
| 4,529,596 A | 7/1985 | Aubert et al. |
| 4,847,265 A | 7/1989 | Badorc et al. |
| 4,927,013 A | 5/1990 | Van Brunt et al. |
| 5,134,127 A | 7/1992 | Stella et al. |
| 5,241,059 A | 8/1993 | Yoshinaga |
| 5,288,726 A | 2/1994 | Koike et al. |
| 5,324,718 A | 6/1994 | Loftsson |
| 5,376,645 A | 12/1994 | Stella et al. |
| 5,436,242 A | 7/1995 | Koike et al. |
| 5,472,954 A | 12/1995 | Loftsson |
| 5,576,328 A | 11/1996 | Herbert et al. |
| 5,632,275 A | 5/1997 | Browne et al. |
| 5,874,418 A | 2/1999 | Stella et al. |
| 5,989,578 A | 11/1999 | Bernat et al. |
| 6,046,177 A | 4/2000 | Stella et al. |
| 6,071,514 A | 6/2000 | Grinnell et al. |
| 6,133,248 A | 10/2000 | Stella |
| 6,153,746 A | 11/2000 | Shah et al. |
| 6,204,256 B1 | 3/2001 | Shalaby et al. |
| 6,248,729 B1 | 6/2001 | Coniglio et al. |
| 6,294,192 B1 | 9/2001 | Patel et al. |
| 6,383,471 B1 | 5/2002 | Chen et al. |
| 6,429,210 B1 | 8/2002 | Bousquet et al. |
| 6,451,339 B2 | 9/2002 | Patel et al. |
| 6,504,030 B1 | 1/2003 | Bousquet et al. |
| 6,509,348 B1 | 1/2003 | Ogletree |
| 6,569,463 B2 | 5/2003 | Patel et al. |
| 6,573,381 B1 | 6/2003 | Bousquet et al. |
| 6,693,115 B2 | 2/2004 | Asai et al. |
| 6,720,001 B2 | 4/2004 | Chen et al. |
| 6,737,411 B2 | 5/2004 | Valeriano et al. |
| 6,761,903 B2 | 7/2004 | Chen et al. |
| 6,767,913 B2 | 7/2004 | Lifshitz et al. |
| 6,800,759 B2 | 10/2004 | Valeriano et al. |
| 6,858,734 B2 | 2/2005 | Silva |
| 6,914,141 B2 | 7/2005 | Sherman |
| 6,923,988 B2 | 8/2005 | Patel et al. |
| 7,018,990 B2 | 3/2006 | Wong et al. |
| 7,034,013 B2 | 4/2006 | Thompson et al. |
| 7,074,928 B2 | 7/2006 | Lifshitz-Liron et al. |
| 7,259,261 B2 | 8/2007 | Valeriano et al. |

(Continued)

FOREIGN PATENT DOCUMENTS

| | | |
|---|---|---|
| CN | 101390856 | 3/2009 |
| EP | 0 579 435 | 1/1994 |
| FR | 2 769 313 | 4/1999 |
| JP | 2002-255814 | 9/2002 |
| KR | 20070034681 | 3/2007 |
| SI | 21748 | 3/2004 |
| WO | WO 91/11172 | 8/1991 |
| WO | WO 94/02518 | 2/1994 |

(Continued)

OTHER PUBLICATIONS

Montalescot, G. et al "Prasugrel compared with clopidogrel in patients . . . " The Lancet (2009) vol. 373, pp. 723-731.*

(Continued)

*Primary Examiner* — Leigh C Maier
(74) *Attorney, Agent, or Firm* — Knobbe Martens Olson & Bear LLP

(57) ABSTRACT

The present invention is directed to pharmaceutical compositions comprising prasugrel and a cyclodextrin derivative, and methods of making and using the same.

22 Claims, 6 Drawing Sheets

(56) References Cited

U.S. PATENT DOCUMENTS

| | | |
|---|---|---|
| 7,329,751 B2 | 2/2008 | Castaldi et al. |
| 7,446,200 B2 | 11/2008 | Deshpande et al. |
| 7,470,707 B2 | 12/2008 | Yun et al. |
| 7,629,331 B2 | 12/2009 | Pipkin et al. |
| 7,635,773 B2 | 12/2009 | Antle |
| 7,799,782 B2 | 9/2010 | Munson et al. |
| 8,236,782 B2 | 8/2012 | Mosher et al. |
| 8,343,995 B2 | 1/2013 | Mosher et al. |
| 2002/0032149 A1 | 3/2002 | Kensey |
| 2003/0104048 A1 | 6/2003 | Patel et al. |
| 2004/0067995 A1 | 4/2004 | Wong et al. |
| 2004/0109888 A1 | 6/2004 | Pun et al. |
| 2004/0115287 A1 | 6/2004 | Chen et al. |
| 2005/0049226 A1 | 3/2005 | Silva |
| 2005/0049275 A1 | 3/2005 | Valeriano et al. |
| 2005/0096296 A1 | 5/2005 | Fikstad et al. |
| 2005/0143414 A1 | 6/2005 | Castaldi et al. |
| 2005/0164986 A1 | 7/2005 | Mosher et al. |
| 2005/0186267 A1 | 8/2005 | Thompson et al. |
| 2005/0203059 A1 | 9/2005 | Harrison et al. |
| 2005/0203122 A1 | 9/2005 | Doser et al. |
| 2005/0228012 A1 | 10/2005 | Yun et al. |
| 2005/0250738 A1 | 11/2005 | Mosher et al. |
| 2005/0256152 A1 | 11/2005 | Doser et al. |
| 2005/0276841 A1 | 12/2005 | Davis et al. |
| 2006/0003002 A1 | 1/2006 | Fikstad et al. |
| 2006/0041136 A1 | 2/2006 | Veverka et al. |
| 2006/0047121 A1 | 3/2006 | Sawant et al. |
| 2006/0074242 A1 | 4/2006 | Deshpande et al. |
| 2006/0100231 A1 | 5/2006 | Parthasaradhi et al. |
| 2006/0134206 A1 | 6/2006 | Iyer et al. |
| 2006/0154957 A1 | 7/2006 | Finkelstein et al. |
| 2006/0223845 A1 | 10/2006 | Turgeman et al. |
| 2007/0003615 A1 | 1/2007 | Jenkins et al. |
| 2007/0020196 A1 | 1/2007 | Pipkin et al. |
| 2007/0037842 A1 | 2/2007 | Lohray et al. |
| 2008/0108589 A1 | 5/2008 | Asai et al. |
| 2008/0113000 A1 | 5/2008 | Hunter et al. |
| 2008/0176893 A1 | 7/2008 | Dziennik et al. |
| 2008/0200533 A1 | 8/2008 | Krishnan |
| 2008/0220441 A1 | 9/2008 | Birnbaum et al. |
| 2009/0012042 A1 | 1/2009 | Ren et al. |
| 2009/0123540 A1 | 5/2009 | Pipkin et al. |
| 2009/0270348 A1 | 10/2009 | Antle |
| 2010/0093664 A1 | 4/2010 | Rowe |
| 2013/0045251 A1* | 2/2013 | Cen et al. ......... A61K 31/4365 424/400 |

FOREIGN PATENT DOCUMENTS

| | | |
|---|---|---|
| WO | WO 97/29753 | 8/1997 |
| WO | WO 99/42111 | 8/1999 |
| WO | WO 03/002152 | 1/2003 |
| WO | WO 03/066637 | 8/2003 |
| WO | WO 2004/098713 | 11/2004 |
| WO | WO 2005/065649 | 7/2005 |
| WO | WO 2005/117911 | 12/2005 |
| WO | WO 2006/138317 | 12/2006 |
| WO | WO 2007/024472 | 3/2007 |
| WO | WO 2008/060934 | 5/2008 |
| WO | WO 2008/072836 | 6/2008 |
| WO | WO 2008/072939 | 6/2008 |
| WO | WO 2008/073759 | 6/2008 |
| WO | WO 2008/108291 | 9/2008 |
| WO | WO 2008/134600 | 11/2008 |
| WO | WO 2008/134601 | 11/2008 |
| WO | WO 2009/018069 | 2/2009 |
| WO | WO 2009/054095 | 4/2009 |
| WO | WO 2010/009335 | 1/2010 |

OTHER PUBLICATIONS

Strickley, R. "Solubilizing excipients in oral and injectable formulations" Pharm. Res. (2004) vol. 21, No. 2, pp. 201-230.*

Dyszkiewicz-Korpantry et al., 2005, Approach to the assessment of platelet function: comparison between optical-based platelet-rich plasma and impedance-based whole blood platelet aggregation methods, Clin. Appl. Thromb. Hemost. 11:25-35.

Fridriksdottir et al., 1997, Formulation and testing of methazolamide cyclodextrin eye drop solutions, Journal of Controlled Release, 44(1):95-99.

Fridriksdottir et al., Jan. 1996, Design and in vivo testing of 17β-estradiol HPβCD sublingual tablets, Die Pharmazie, 51(1):39-42.

Fridriksdottir et al., Mar. 31-Apr. 2, 1996, Solubilization of β-cyclodextrin: the effect of polymers and various drugs on the solubility of β-cyclodextrin, Proceedings of the Eighth International Symposium on Cyclodextrins, eds. Szejtli et al., Budapest, 373-376.

Gurbel et al., 2005, Clopidogrel Loading With Eptifibatide to Arrest the Reactivity of Platelets: Results of the Clopidogrel Loading With Eptifibatide to Arrest the Reactivity of Platelets (Clear Platelets) Study, Circulation 111:1153-1159.

Hennan et al., 1965, Prevention of experimental carotid and coronary artery thrombosis by the glycoprotein IIb/IIIa receptor antagonist CRL42796, Br. J. Pharmacol. 136(6):927-937.

Higuchi et al., 1965, Phase Solubility Techniques, in Advances in Analytical Chemistry and Instrumentation, vol. 4, pp. 117-212, Reilly, C., ed, John Wiley & Sons Inc., United Kingdom.

Kolbe et al., 2002, Preparation and Characterization of Clopidogrel/DIMEB Complex, J. Inclusion Phenomena and Macrocylic Chemistry, 44:183-184.

Kristinsson et al., 1996, Dexamethasone-cyclodextrin-polymer co-complexes in aqueous eye drops, Investigative Ophthalmology & Visual Science, 37(6):1199-1203.

Lammers et al., 1971, Properties of cyclodextrins: Part VI. Water-soluble cyclodextrin-derivatives. Preparation and Analysis, Die Starke, 23(5):167-171.

Lammers et al., 1972, Properties of Cyclodextrins, Part VIII. Determination of the composition of inclusion complexes of hexane and 2,3-dimethylbutane with cyclodextrin derivatives in aqueous solution, Recl. Trav. Chim. Pays-Bas 91:733-742.

Loftsson et al., 1994, The effect of polyvinylpyrrolidone and hydroxypropyl methylcellulose on HPβCD complexation of hydrocortisone and its permeability through hairless mouse skin, European Journal of Pharmaceutical Sciences, 2:297-301.

Loftsson et al., 1994, The effect of water-soluble polymers on drug-cyclodextrin complexation, International Journal of Pharmaceutics (Netherlands), 110(2):169-177.

Loftsson et al., 1996, Effects of cyclodextrins and polymers on topical drug delivery to the eye—evaluations in humans, Proceedings of the 23rd International Symposium on Controlled Release of Bioactive Materials, pp. 453-454.

Loftsson et al., 1996, The influence of water-soluble polymers and pH on hydroxypropyl-β-cyclodextrin complexation of drugs, Drug Development and Industrial Pharmacy, 22(5):401-405.

Loftsson et al., 1997, Cyclodextrins as pharmaceutical excipients, Pharm. Technol. Eur. 9(5):26-34.

Loftsson et al., 1997, Enhanced complexation efficiency of cyclodextrins, Pharmaceutical Research, 14(11):S203.

Loftsson et al., 1998, Cyclodextrin solubilization of ETH-615, a zwitterionic drug, Drug Development and Industrial Pharmacy, 24(4):365-370.

Loftsson et al., 1998, The effect of water-soluble polymers on the aqueous solubility and complexing abilities of β-cyclodextrin, International Journal of Pharmaceutics, 163(1-2):115-121.

Loftsson et al., 1999, Methods to enhance the complexation efficiency of cyclodextrins, S.T.P. Pharma Sciences, 9(3):237-242.

Loftsson et al., 2001, Cyclodextrin solubilization of benzodiazepines: formulation of midazolam nasal spray, International Journal of Pharmaceutics, 212(1):29-40.

Loftsson et al., Apr. 11, 1994, The effect of hydroxypropyl methylcellulose on the release of dexamethasone from aqueous 2-hyroxypropyl-β-cyclodextrin formulations, International Journal of Pharmaceutics (Netherlands), 104:181-184.

Loftsson et al., Oct. 1994, Polymer-cyclodextrin-drug complexes, Pharmaceutical Research, 11(10):S225.

(56) References Cited

OTHER PUBLICATIONS

Loftsson et al., Oct. 1996, Pharmaceutical applications of cyclodextrins. 1. Drug solubilization and stabilization, Journal of Pharmaceutical Sciences, 85(10):1017-1025.
Loftsson et al., Sep. 16, 1996, Drug-cyclodextrin-polymer ternary complexes, European Journal of Pharmaceutical Sciences, 4(Suppl):S144.
Loftsson et al., Sep. 1996, Solubilization of β-cyclodextrin, Eur. J. Pharm. Sci, 4(Suppl.):S143.
Loftsson et al., Sep. 2001, Sustained drug delivery system based on a cationic polymer and an anionic drug/cyclodextrin complex, Pharmazie, 56(9):746-747.
Loftsson, 1996, Topically effective acetazolamide eye-drop solution in man, Pharmaceutical Sciences, 2(6):277-279.
Loftsson, 1998, Drug-cyclodextrin complexation in the presence of water soluble polymers: enhanced solubility and percutaneous transport, Abstracts of Papers Part 1, 216th ACS National Meeting, Boston, Aug. 23-27, CELL-016.
Loftsson, Apr. 2-6, 1995, The effect of polymers on cyclodextrin complexation, Book of Abstracts, 209th ACS National Meeting, 209(1):33-CELL.
Masson et al., 1999, Drug-cyclodextrin complexation in the presence of water-soluble polymers: enhanced solubility and percutaneous transport, ACS Symposium Series, 737 (Polysaccharide Applications), pp. 24-45.
Mehta et al., 2001, Effects of pretreatment with clopidogrel and aspirin followed by long-term therapy in patients undergoing percutaneous coronary intervention: the PCI-CURE study, The Lancet, 358:527-533.
Niitsu et al., Jan. 2008, Repeat oral dosing of prasugrel, a novel $P2Y_{12}$ receptor inhibitor, results in cumulative and potent antiplatelet and antithrombotic activity in several animal species, European Journal of Pharmacology, 579:276-282.
Pereillo et al., 2002, Structure and stereochemistry of the active metabolite of clopidogrel, Drug Metab. Disposition, 30(11):1288-1295.
Physician's Desk Reference, 2002, PLAVIX.RTM., Murray et al., eds, Medical Economics Company, Inc., Montvale, NJ, pp. 3084-3086.
Pickard et al., Mar. 2008, Clopidogrel-Associated Bleeding and Related Complications in Patients Undergoing Coronary Artery Bypass Grafting, Pharmacotherapy, 28:376-392.
Polymer Science, in Physical Pharmacy. Physical Chemical Principles in Pharmaceutical Sciences, 3rd edition, Martin et al., 1983, pp. 592-638.
Polymers and Macromolecules, in Physicochemical Principles of Pharmacy, 2nd edition, Florence et al., eds. pp. 281-334, 1988.
Qu, Q., et al., "Sulfoalkyl Ether .beta.-Cyclodextrin Derivatives: Synthesis and Characterizations," J. Inclusion Phenomena Macro. Chem. 43: 213-221, Kluwer Academic Publishers, Netherlands (2002).
Reist et al., 2000, Very Slow Chiral Inversion of Clopidogrel in Rats: A Pharmacokinetic and Mechanistic Investigation, Drug Metab. Disposition 28(12):1405-1410.
Remington's Pharmaceutical Sciences, 18th Edition, Gennaro ed., 1990, Hydrophilic Dispersons, pp. 291-294.
Savolainen et al., 1998, Co-administration of a water-soluble polymer increases the usefulness of cyclodextrins in solid oral dosage forms, Pharmaceutical Research, 15(11):1696-1701.
Savolainen et al., May 31-Jun. 3, 1998, Coadministration of a water-soluble polymer increases the usefulness of cyclodextrins in solid oral dosage forms, 9th Proceedings of the International Symposium on Cyclodextrins, Santiago de Comostela, Spain, eds. Labandeira et al., pp. 261-264.
Schafer et al., 2009, Critical Review of Prasugrel for Formulary Decision Makers, Journal of Managed Care Pharmacy, 15(4):335-343.
Serebruany, 2009, Platelet Inhibition with Prasugrel and Increased Cancer Risks: Potential Causes and Implications, The American Journal of Medicine 122(5):407-408.
Siddique et al., May 2009, New antiplatelet drugs: beyond aspirin and clopidogrel, Int. J. Clin. Pract. 63(5):776-789.
Sigurdardottir et al., Dec. 29, 1995, The effect of polyvinylpyrrolidone on cyclodextrin complexation of hydrocortisone and its diffusion through hairless mouse skin, International Journal of Pharmaceutics (Netherlands), 126:73-78.
Small et al., 2008, Effect of ranitidine on the pharmacokinetics and pharmacodynamics of prasugrel and clopidogrel, Curr. Med. Res. Opin., 24(8):2251-2257.
Smith et al., 2007, Disposition and metabolic fate of prasugrel in mice, rats, and dogs, Xenobiotica 37(8):884-901.
Sramek et al., 1992, A Randomized and Blinded Comparison of Three Bleeding Time Techniques: the Ivy Method, and the Simplate II Method in Two Directions, Thromb. Haemost. 67(5):514-518.
von Beckerath et al., 2005, Absorption, Metabolization, and Antiplatelet Effects of 300-, 600-, and 900-mg Loading Doses of Clopidogrel: Results of the ISAR-CHOICE (Intracoronary Stenting and Antithrombic Regimen: Choose Between 3 High Oral Doses for Immediate Clopidrogrel Effect) Trial., Circulation, 112:2946-2950.
Waehre et al., 2006, Clopidogrel increases expression of chemokines in peripheral blood mononuclear cells in patients with coronary artery disease: results of a double-blind placebo-controlled study, Journal of Thrombosis and Haemostatis, 4(10):2140-2147 (abstract).
Wedel et al., Nov. 9-15, 2007, Effects of Modified Cyclodextrin Derivatives on the Solubility and Stability of Clopidogrel Bisulfate in Aqueous Formulations, 2007 AAPS Annual Meeting & Exposition, retrieved from the internet: URL:http://abstracts.aapspharmaceutica.com/ExpoAAPS07/CC/forms/attendee/i-ndex.aspx?content=sessionInfo&sessionId=1153.
Weerakkody et al., Jul. 2007, Comparison of speed of onset of platelet inhibition after loading doses of clopidogrel versus prasugrel in healthy volunteers and correlation with responder status, Am. J. Cardiol. 100:331-336.
Weerakkody et al., Sep. 2007, Greater Inhibition of Platelet Aggregation and Reduced Response Variability with Prasugrel Versus Clopidogrel: An Integrated Analysis, J. Cardiovasc. Pharmacol. Ther., 12(3):205-212.
Wegert et al., 2002, Effects of antiplatelet agents on platelet-induced thrombin generation, Int. J. Clin. Pharmacol. Ther., 40(4):135-141.
Wiviott et al., Nov. 15, 2007, Prasugrel versus Clopidogrel in Patients with Acute Coronary Syndromes, N. Engl. J. Med., 357(20):2001-2015.
International Search Report for International Application No. PCT/US2010/034800, United States Patent and Trademark Office, United States, mailed on Jul. 29, 2010.

* cited by examiner

PHARMACEUTICAL COMPOSITIONS COMPRISING PRASUGREL AND CYCLODEXTRIN DERIVATIVES AND METHODS OF MAKING AND USING THE SAME

CROSS-REFERENCE TO RELATED APPLICATIONS

This application is a continuation application of U.S. patent application Ser. No. 13/542,253, filed Jul. 5, 2012, which is a continuation of U.S. patent application Ser. No. 12/779,850, filed May 13, 2010, now U.S. Pat. No. 8,236,782, which claims the benefit of U.S. Provisional Application No. 61/177,718, filed May 13, 2009. The contents of all the foregoing patent applications are hereby incorporated by reference in their entireties.

BACKGROUND OF THE INVENTION

1. Field of the Invention

The present invention relates to pharmaceutical compositions comprising prasugrel and a cyclodextrin derivative, and methods of making and using the same, for example, to treat disorders and diseases that are therapeutically responsive to prasugrel.

2. Background of the Invention

Platelets play a central role in the pathogenesis of atherothrombosis and in the formation of thrombi following coronary angioplasty, with and without stent implantation. Platelets initially adhere at sites of vascular injury, atherosclerotic plaque rupture, balloon angioplasty, and stenting. Platelet activation following these interactions results in the release of adenosine diphosphate ("ADP"), thromboxane A2, and other mediators. Released ADP promotes platelet activation via the G-protein linked $P2Y_1$ and $P2Y_{12}$ purinergic receptors leading to further platelet activation, aggregation, and other platelet functions, such as platelet shape change, secretion, and the development of pro-coagulant and pro-inflammatory activities. Activated platelets are recruited to sites of coronary plaque rupture and intra-arterial stenting, thereby forming aggregates that may lead to platelet-rich thrombi, vascular occlusion, tissue ischemia, and myocardial necrosis in what is collectively known as Acute Coronary Syndrome ("ACS"). The term ACS is a pathophysiological continuum progressing from ischemic chest pain with sudden onset and worsening, to ischemia severe enough to cause irreversible myocardial damage detected with cardiac biomarkers without persistent ST-segment elevation, to total occlusion of the culprit coronary artery with persistent ST-segment elevation, resulting in myocardial necrosis and elevated biomarkers. ACS occurs in a diverse global population and has a significant socioeconomic impact as subjects require hospitalization, rehabilitation, and often suffer subsequent ischemic events.

Options for the initial management of ACS include pharmacotherapy alone or an early invasive strategy with percutaneous coronary intervention ("PCI," with or without coronary stenting) or coronary artery bypass grafting (CABG) as guided by the results of coronary angiography. The current American College of Cardiology/American Heart Association and European Society of Cardiology guidelines recommend an early invasive strategy for ACS subjects with intermediate to high-risk features. Pharmacotherapy includes both anticoagulant and anti-platelet drugs. The current standard of care for subjects with ACS includes dual anti-platelet therapy with aspirin and thienopyridine in both the acute and chronic phases of treatment. This therapy improves outcome in subjects with ACS and those undergoing PCI; the high risk of early stent-associated thrombosis is substantially reduced by dual antiplatelet therapy. Ticlopidine and clopidogrel are the two currently approved thienopyridines. Due to its once-daily dosing regimen, clopidogrel is the predominantly prescribed therapeutic agent to treat subjects suffering from ACS.

Several potential limitations of clopidogrel therapy have been identified despite the loading dose of clopidogrel. This includes marked inter-individual variability in platelet inhibition and relatively slow onset of action. An association between thrombotic complications following PCI and poor antiplatelet response to the approved standard clopidogrel dosing regimen (loading dose ("LD") 300 mg and maintenance dose ("MD") 75 mg) has been suggested. Further, it has been shown that "nonresponsiveness" to a clopidogrel 600 mg LD is a strong predictor of stent thrombosis hi subjects receiving drug-eluting stents, and in addition, that residual platelet aggregation above the median is associated with a 6.7-fold increased risk of major adverse cardiac events (death, myocardial infarction and target vessel revascularisation) at 1 month follow-up in subjects undergoing elective PCI. These observations suggest the possibility that higher and more consistent levels of platelet inhibition may improve clinical outcome in subjects with ACS undergoing PCI.

Prasugrel is a thienopyridine ADP receptor antagonist that can be orally or parenterally administered, and has the chemical name 5-[(1RS)-2-cyclopropyl-1-(2-fluorophenyl)-2-oxoethyl]-4,5,6,7-tetrahydrothieno[3,2-c]pyridin-2-yl acetate (chemical formula: $C_{20}H_{20}FNO_3S$; molecular weight 373.44 g/mol). Clinical testing of prasugrel has utilized a racemic mixture of the hydrochloride salt, which is a white to light brown crystalline solid that is slightly hygroscopic. Prasugrel hydrochloride is soluble to slightly soluble at pH 1-4, very slightly soluble at pH 5 and practically insoluble at pH 6-7. The $pK_a$ value of prasugrel hydrochloride is 5.1. Prasugrel is also known to demonstrate polymorphism.

Prasugrel undergoes in vivo metabolism via hydrolysis by carboxylesterases and then multiple cytochrome P450 enzymes to form an active metabolite that irreversibly inhibits platelet activation and aggregation mediated by the $P2Y_{12}$-receptor. Once bound, a platelet is inhibited for its remaining lifespan. After prasugrel dosing is stopped, a return to baseline levels of platelet aggregation will occur as new platelets are formed, a process that typically occurs over about 7-10 days after treatment is stopped.

Non-clinical studies indicate that, with respect to inhibiting ex vivo platelet aggregation and in vivo thrombus formation, prasugrel was approximately 10-fold to 100-fold more potent than clopidogrel and ticlopidine, respectively. Prasugrel compositions, dosage forms, and methods of treatment using the same are known. See, e.g., U.S. Pat. Nos. 5,288,726, 5,436,242 and 6,693,115, U.S. Patent Pub. Nos. 2008/0108589 and 2008/0176893, and WO 2004/098713, WO 2006/138317 and WO 2008/073759, which are incorporated herein by reference in the entirety. Clinical data in healthy subjects has confirmed the greater platelet inhibition and more consistent response to prasugrel compared to clopidogrel. While the active metabolites of prasugrel and clopidogrel resulted in similar levels of platelet inhibition in vitro, the amount of each active metabolite generated in vivo differs significantly: a prasugrel loading dose of 60 mg results in approximately a 50-fold greater exposure, on a per milligram basis, to its active metabolite compared to a clopidogrel loading dose of 300 mg.

Compositions comprising clopidogrel and a cyclodextrin derivative are known. See, e.g., U.S. Pat. No. 5,989,578, WO 2008/072836, WO 2008/134600 and WO 2008/134601, which are incorporated herein by reference in the entirety.

Prasugrel has completed at least one clinical trial relating to treating subjects suffering from acute coronary syndromes who have undergone a percutaneous coronary intervention or for whom a percutaneous coronary intervention is planned. See, e.g., Wiviott, S. D. et al., *N. Engl. J. Med.* 357:2001 (2007). Acute coronary syndrome includes heart attacks and unstable angina (chest pain). Prasugrel has demonstrated a reduction in the combined rate of death from cardiovascular causes and nonfatal myocardial infarction, as well as nonfatal stroke compared to clopidogrel. However, subjects administered prasugrel have also exhibited an increased rate of serious bleeding events. In the clinical trial, three subgroups had less efficacy and greater absolute levels of bleeding than the overall treatment group, resulting in a reduced net clinical benefit or in clinical harm. The risk of bleeding related adverse effects was most evident in patients with a history of stroke or transient ischemic attack before enrollment, the elderly (subjects 75 years of age and older), and subjects having a body mass less than 60 kg. It was postulated that the increased risk of bleeding in elderly subjects and subjects having a body mass less than 60 kg may have been due to increased levels of the active metabolite, arising from an altered disposition to the drug and/or a smaller body size.

BRIEF SUMMARY OF THE INVENTION

What is needed is a prasugrel formulation that can minimize the toxicology and side-effect profile of prasugrel, for example, by providing a prasugrel formulation that can be titrated more safely and/or easily to a therapeutically effective dosage, by providing increased bioavailability of the active species, and/or by providing an improved rate of therapeutic onset. As described herein, compositions suitable for oral or parenteral administration that include prasugrel and a cyclodextrin have been developed.

The present invention is directed to a pharmaceutical composition comprising prasugrel and a cyclodextrin derivative of formula I:

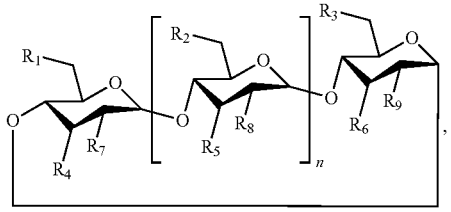

I wherein n is 4, 5 or 6, wherein $R_1$, $R_2$, $R_3$, $R_4$, $R_5$, $R_6$, $R_7$, $R_8$ and $R_9$ are independently selected from: —OH, a straight-chain or branched —O—($C_1$-$C_8$-(alkylene))-$SO_3^-$ group, an optionally substituted straight-chain, branched, or cyclic —O—($C_1$-$C_{10}$) group, an optionally substituted straight-chain, branched, or cyclic —S—($C_1$-$C_{10}$) group, and a saccharide, and wherein the cyclodextrin derivative is present in a concentration of at least 100:1 by weight relative to the prasugrel.

In some embodiments, the cyclodextrin derivative is present in a concentration of at least 50:1 by mole relative to the prasugrel.

In some embodiments, a pharmaceutical composition has a pH of about 2 to about 4, and the cyclodextrin derivative is present in a ratio of about 100:1 to about 700:1 by weight relative to the prasugrel.

In some embodiments, a pharmaceutical composition has a pH of about 4 to about 9, and the cyclodextrin derivative is present in a ratio of at least 700:1 by weight relative to the prasugrel.

In some embodiments, at least one of $R_1$, $R_2$, $R_3$, $R_4$, $R_5$, $R_6$, $R_7$, $R_8$ and $R_9$ is a —O-(hydroxy-substituted-$C_3$) group.

In some embodiments, $R_1$, $R_2$, $R_3$, $R_4$, $R_5$, $R_6$, $R_7$, $R_8$ and $R_9$ are independently a straight-chain or branched —O—($C_1$-$C_8$-(alkylene))-$SO_3^-$ group having a degree of substitution of about 4 to about 8 per cyclodextrin derivative, and the remaining substituents are —H.

In some embodiments, at least one of $R_1$, $R_2$, $R_3$, $R_4$, $R_5$, $R_6$, $R_7$, $R_8$ and $R_9$ is substituted with a —O-(straight-chain $C_4$-(alkylene))-$SO_3^-$ group.

In some embodiments, the cyclodextrin derivative is a compound of formula II:

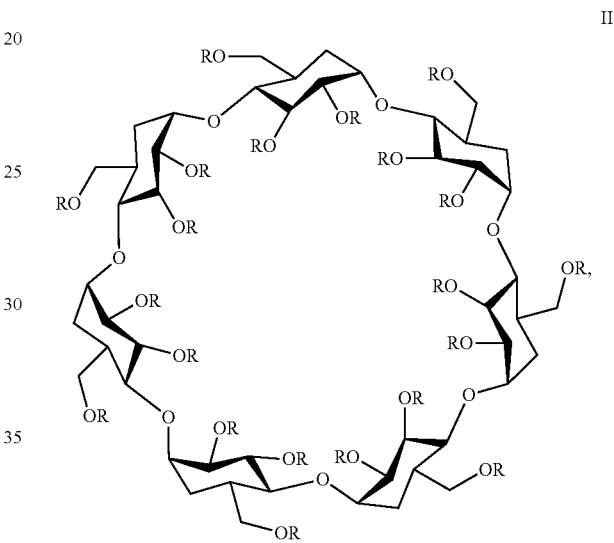

II wherein R=$(H)_{21-x}$ or $(—(CH_2)_4—SO_3^-Na^+)_x$. In some embodiments, x=6.0-7.1.

In some embodiments, the pharmaceutical composition of the present invention comprises an agent selected from: a carrier, a preservative, an antioxidant, a second therapeutic agent, an acidifying agent, an alkalinizing agent, a buffering agent, a bulking agent, a complexation enhancing agent, a cryoprotectant, a density modifier, an electrolyte, a flavor, a fragrance, a lyophilizing aid, a plasticizer, a solubility-enhancing agent, a stabilizing agent, a sweetener, a surface tension modifier, a volatility modifier, a viscosity modifier, and combinations thereof.

In some embodiments, the pharmaceutical composition of the present invention comprises a nonsteroidal antiinflammatory drug, a selective factor Xa inhibitor, a direct thrombin inhibitor, a prostaglandin analog, an adenosine diphosphate (ADP) inhibitor, a platelet aggregation inhibitor, an antiplatelet agent, a glycoprotein IIb/IIIa inhibitor or antagonist, an antisickling agent, a hemorrheologic agent, a thrombolytic agent, a thrombolytic enzyme, a thromboxane A2 biosynthesis inhibitors, a thromboxane antagonist, a cyclooxygenase inhibitor, an angiotensin antagonist, an endothelin antagonist, a phosphodiesterase inhibitor, an angiotensin converting enzyme (ACE) inhibitors, a neutral endopeptidase inhibitors, an anticoagulants, a diuretic, a tissue plasminogen activator, a modified tissue plasminogen activator, a biologic response modifier, a statin, a calcium channel blocking agent, an antiarrhythmic agent, an α-adrenergic agonist, a β-adrenergic antagonist, or a combination thereof.

In some embodiments, the pharmaceutical composition of the present invention comprises a second therapeutic agent selected from: an analog or derivative of prasugrel, clopidogrel, diclofenac, droxicam, etolodac, fenoprofen, flurbiprofen, indomethacin, isoxicam, ketoprofen, lornoxicam, meloxicam, mefenamate, naproxen, oxaprozin, piroxicam, sulindac, tenoxicam, apixaban, otamixaban, rivaroxaban, eptifibatide, beraprost, prostacyclin, iloprost, treprostinil, ticagrelor, ticlopidine, abciximab, cloricromen, ditazole, indobufen, picotamide, sulfinpyrazone, abciximab, eptifibatide, tirofiban, cetiedil, alteplase, anistreplase, brinase, drotrecogin alfa, monteplase, reteplase, saruplase, streptokinase, tenecteplase, urokinase, fibrinolysin, ancrod, aspirin, picotamide, ramatroban, seratrodast, aloxiprin, carbasalate calcium, celecoxib, ibuprofen, rofecoxib, candesartan, eprosartan, irbesartan, losartan, olmesartan, telmisartan, valsartan, ambrisentan, atrasentan, bosentan, sitaxentan, tezosentan, cilostazol, dipyridamole, enoximone, milrinone, captopril, enalapril, enaliprilat, spirapril, quinapril, perindopril, ramipril, fosinopril, trandolapril, lisinopril, moexipril, benazapril, candoxatril, ecadotril, candoxatril, ecadotril, unfractionated heparin, ardeparin, bemiparin, certoparin, dalteparin, enoxaparin, fondaparin, fragmin, melagatran, nadroparin, parnaparin, reviparin, tinzaparin, argatroban, dabigatran, melagatran, ximelagatran, defibrotide, ramatroban, antithrombin III, fondaparinux, idraparinux, danaparoid, sulodexide, dermatan sulfate, a synthetic pentasaccharide, a hirudin, disulfatohirudin bivalirudin, desirudin, lepirudin, acenocoumarol, coumatetralyl, dicoumarol, ethyl biscoumacetate, phenprocoumon, clorindione, diphenadione, phenindione, tioclomarol, warfarin, chlorothiazide, hydrochlorothiazide, ethacrynic acid, furosemide, amiloride, chlorothiazide, hydrochlorothiazide, atorvastatin, fluvastatin, lovastatin, pravastatin, pravastatin, rosuvastatin, simvastatin, amlodipine, felodipine, diltiazem, nifedipine, nicardipine, nisoldipine, bepridil, verapamil, dofetilide, ibutilide, metoprolol, propranolol, atenolol, betaxolol, bisoprolol, carvediol, nadolol, nebivolol, timolol, ajmaline, disopyramide, prajmaline, procainamide, quinidine, sparteine, aprindine, lidocaine, mexiletine, tocainide, encainide, flecainide, lorcainide, moricizine, propafenone, acebutolol, pindolol, amiodarone, bretylium, bunaftine, dofetilide, sotalol, adenosine, atropine, digoxin, doxazosin, terazosin, prazosin, and combinations thereof.

The present invention is also directed to a unit dosage form comprising about 1 mg to about 120 mg prasugrel and a cyclodextrin derivative of formula I:

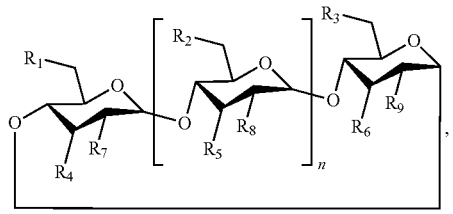

wherein n is 4, 5 or 6, wherein $R_1$, $R_2$, $R_3$, $R_4$, $R_5$, $R_6$, $R_7$, $R_8$ and $R_9$ are independently selected from: —OH, a straight-chain or branched —O—$(C_1$-$C_7$-(alkylene))-$SO_2^-$ group, an optionally substituted straight-chain, branched, or cyclic —O—$(C_1$-$C_{10})$ group, an optionally substituted straight-chain, branched, or cyclic —S—$(C_1$-$C_{10})$ group, and a saccharide, and wherein the cyclodextrin derivative is present in a concentration of at least 100:1 by weight relative to the prasugrel.

In some embodiments, the unit dosage form comprises about 1 mg to about 20 mg of prasugrel. In some embodiments, a unit dosage form comprises about 20 mg to about 120 mg of prasugrel.

In some embodiments, the unit dosage form is a solid. In some embodiments, the solid unit dosage form is a lyophilized solid or an aseptic spray-dried solid.

In some embodiments, the unit dosage form of the present invention comprises prasugrel in a concentration of about 0.005% to about 2% w/v, a cyclodextrin derivative in a concentration of about 5% to about 40% w/v, and the unit dosage form is an aqueous solution having a pH of about 2 to about 4.

In some embodiments, the unit dosage form of the present invention comprises a 0.1 M buffer, wherein the prasugrel in the unit dosage form degrades by 10% or less over a period of 24 hours.

In some embodiments, the unit dosage form of the present invention comprises prasugrel in a concentration of about 0.005% to about 1% w/v, a cyclodextrin derivative in a concentration of about 5% to about 40% w/v, and the unit dosage form is an aqueous solution having a pH of about 4 to about 9.

In some embodiments, the unit dosage form of the present invention comprises a 0.1 M buffer, wherein the prasugrel in the unit dosage form degrades by 20% or less over a period of 24 hours.

The present invention is also directed to a method of treating a subject in need thereof, comprising orally or parenterally administering a unit dosage form of the present invention to the subject in need thereof.

In some embodiments, the method of the present invention comprises diluting a unit dosage form of the present invention with an aqueous carrier, and then parenterally administering the diluted unit dosage form.

In some embodiments, the method of the present invention comprises administering a unit dosage form selected from: a concentrated liquid unit dosage, a lyophilized solid unit dosage, an aseptic spray-dried solid unit dosage, and a reconstitutable unit dosage.

The present invention is also directed to a method of decreasing the time to therapeutic onset of prasugrel following administration thereof, the method comprising orally or parenterally administering to a subject in need thereof a pharmaceutical composition of the present invention, wherein the time to therapeutic onset of prasugrel provided by the orally or parenterally administered composition is less than the time to therapeutic onset of prasugrel provided by an orally administered reference composition that excludes the cyclodextrin derivative and contains an equivalent dose of prasugrel.

The present invention is also directed to a method of treating a disease, disorder or condition having an etiology associated with platelet aggregation or of a disease, disorder or condition that is therapeutically responsive to prasugrel, the method comprising administering to a subject in need thereof a pharmaceutical composition of the present invention.

In some embodiments, the present invention is directed to a method for titrating a subject in need thereof to a therapeutically effective dose of prasugrel, the method comprising: parenterally administering a first dose of the pharmaceutical composition of the present invention to the subject in need thereof; determining the subject's responsiveness to the first dose of the pharmaceutical composition; and parenterally administering a second dose of the pharmaceutical composition to the subject, wherein the second dose comprises an increased or decreased amount of prasugrel compared to the first dose. In some embodiments, the method comprises: repeating the determining, and parenterally administering further doses of the pharmaceutical composition of the present invention until a desired therapeutic effectiveness is achieved. In some embodiments, a method of the present invention comprises administering a maintenance dose of about 1 mg to about 20 mg of prasugrel.

In some embodiments, the method of the present invention comprises administering a loading dose comprising about 20 mg to about 120 mg of prasugrel.

In some embodiments, the method of the present invention comprises treating a subject that suffers from a disease, disorder or condition selected from: an acute coronary syndrome (e.g., unstable angina/non-Q-wave myocardial infarction, heart attack, angina, and the like), a recent myocardial infarction, a recent stroke, an established peripheral arterial disease, ST-segment elevation acute myocardial infarction, non-ST-segment elevation acute coronary syndrome, a recent percutaneous coronary intervention, a recent angioplasty, a thromboembolism, a pulmonary embolism, a deep vein thrombosis, atherosclerosis, diabetes mellitus, a transient ischemic event, a secondary ischemic event, vascular death with established peripheral arterial disease, cardiovascular disease, cerebrovascular disease, angina pectoris, cardiac arrhythmia, sickle cell crisis, and combinations thereof.

In some embodiments, the method of the present invention comprises administering to a subject a nonsteroidal antiinflammatory drug, a selective factor Xa inhibitor, a direct thrombin inhibitor, a prostaglandin analog, an adenosine diphosphate (ADP) inhibitor, a platelet aggregation inhibitor, an antiplatelet agent, a glycoprotein inhibitor or antagonist, an antisickling agent, a hemorrheologic agent, a thrombolytic agent, a thrombolytic enzyme, a thromboxane A2 biosynthesis inhibitors, a thromboxane antagonist, a cyclooxygenase inhibitor, an angiotensin antagonist, an endothelin antagonist, a phosphodiesterase inhibitor, an angiotensin converting enzyme (ACE) inhibitors, a neutral endopeptidase inhibitors, an anticoagulants, a diuretic, a tissue plasminogen activator, a modified tissue plasminogen activator, a biologic response modifier, a statin, a calcium channel blocking agent, an antiarrhythmic agent, an α-adrenergic agonist, a β-adrenergic antagonist, or a combination thereof.

In some embodiments, the method of the present invention comprises administering to a subject a second therapeutic agent selected from: an analog or derivative of prasugrel, clopidogrel, diclofenac, droxicam, etolodac, fenoprofen, flurbiprofen, indomethacin, isoxicam, ketoprofen, lornoxicam, meloxicam, mefenamate, naproxen, oxaprozin, piroxicam, sulindac, tenoxicam, apixaban, otamixaban, rivaroxaban, eptifibatide, beraprost, prostacyclin, iloprost, treprostinil, ticagrelor, ticlopidine, abciximab, cloricromen, ditazole, indobufen, picotamide, sulfinpyrazone, abciximab, eptifibatide, tirofiban, cetiedil, alteplase, anistreplase, brinase, drotrecogin alfa, monteplase, reteplase, saruplase, streptokinase, tenecteplase, urokinase, fibrinolysin, ancrod, aspirin, picotamide, ramatroban, seratrodast, aloxiprin, carbasalate calcium, celecoxib, ibuprofen, rofecoxib, candesartan, eprosartan, irbesartan, losartan, olmesartan, telmisartan, valsartan, ambrisentan, atrasentan, bosentan, sitaxentan, tezosentan, cilostazol, dipyridamole, enoximone, milrinone, captopril, enalapril, enaliprilat, spirapril, quinapril, perindopril, ramipril, fosinopril, trandolapril, lisinopril, moexipril, benazapril, candoxatril, ecadotril, candoxatril, ecadotril, unfractionated heparin, ardeparin, bemiparin, certoparin, dalteparin, enoxaparin, fondaparin, fragmin, melagatran, nadroparin, parnaparin, reviparin, tinzaparin, argatroban, dabigatran, melagatran, ximelagatran, defibrotide, ramatroban, antithrombin III, fondaparinux, idraparinux, danaparoid, sulodexide, dermatan sulfate, a synthetic pentasaccharide, a hirudin, disulfatohirudin bivalirudin, desirudin, lepirudin, acenocoumarol, coumatetralyl, dicoumarol, ethyl biscoumacetate, phenprocoumon, clorindione, diphenadione, phenindione, tioclomarol, warfarin, chlorothiazide, hydrochlorothiazide, ethacrynic acid, furosemide, amiloride, chlorothiazide, hydrochlorothiazide, atorvastatin, fluvastatin, lovastatin, pravastatin, pravastatin, rosuvastatin, simvastatin, amlodipine, felodipine, diltiazem, nifedipine, nicardipine, nisoldipine, bepridil, verapamil, dofetilide, ibutilide, metoprolol, propranolol, atenolol, betaxolol, bisoprolol, carvediol, nadolol, nebivolol, timolol, ajmaline, disopyramide, prajmaline, procainamide, quinidine, sparteine, aprindine, lidocaine, mexiletine, tocainide, encainide, flecainide, lorcainide, moricizine, propafenone, acebutolol, pindolol, amiodarone, bretylium, bunaftine, dofetilide, sotalol, adenosine, atropine, digoxin, doxazosin, terazosin, prazosin, and combinations thereof.

Further embodiments, features, and advantages of the present inventions, as well as the composition, structure and operation of the various embodiments of the present invention, are described in detail below with reference to the accompanying drawings.

BRIEF DESCRIPTION OF THE FIGURES

The accompanying drawings, which are incorporated herein and form a part of the specification, illustrate one or more embodiments of the present invention and, together with the description, further serve to explain the principles of the invention and to enable a person skilled in the pertinent art to make and use the invention.

DETAILED DESCRIPTION OF THE INVENTION

Figure 1:
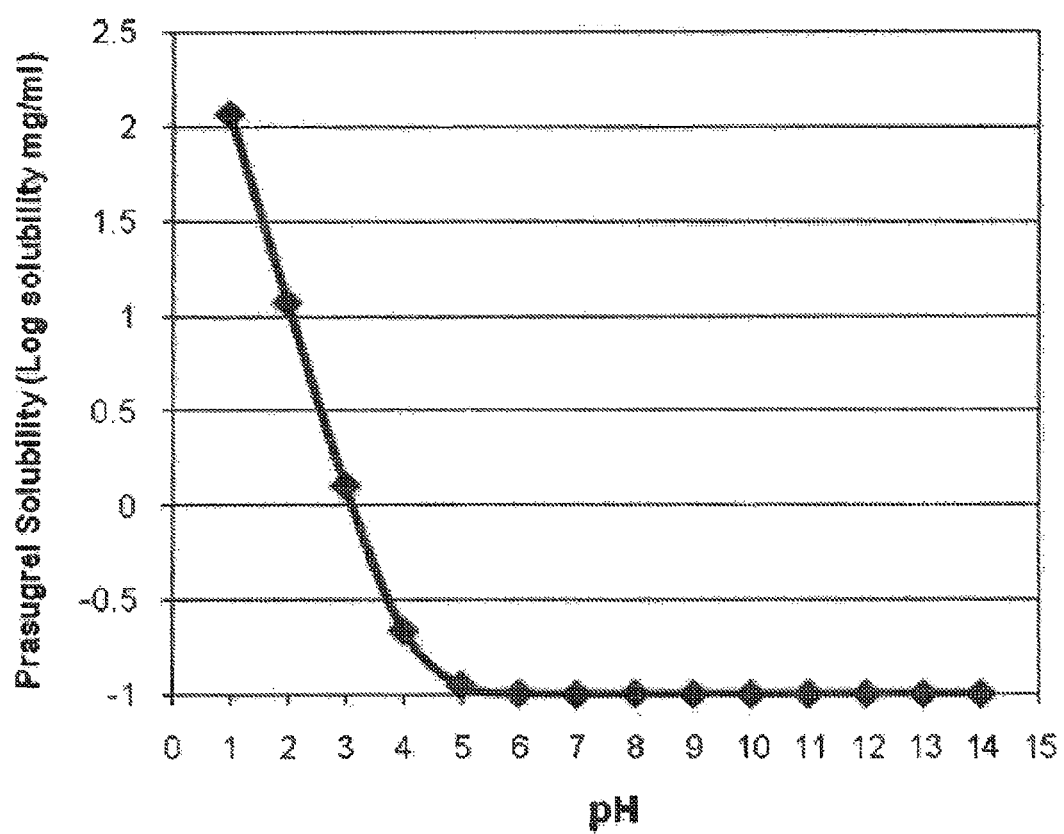
FIG. 1 provides a graphic representation of the theoretical solubility profile of prasugrel as a function of pH, as determined using the generalized solubility equation.

The invention includes combinations and sub-combinations of the various aspects and embodiments disclosed herein. Further, when a particular feature, structure, or characteristic is described in connection with an embodiment, it is understood that it is within the knowledge of one skilled in the art to effect such feature, structure, or characteristic in connection with other embodiments whether or not explicitly described. These and other aspects of this invention will be apparent upon reference to the following detailed description, examples, claims and attached figures.

Prasugrel

The compositions, formulations and unit dosage forms of the present invention comprise prasugrel, which has the following chemical structure:

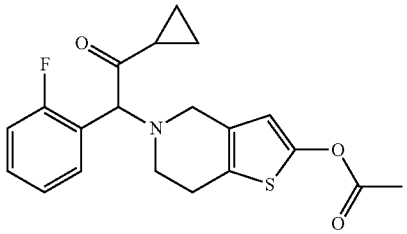

As used herein, the term "prasugrel" refers to the above compound, 5-[(1RS)-2-cyclopropyl-1-(2-fluorophenyl)-2-oxoethyl]-4,5,6,7-tetrahydrothieno[3,2-c]pyridin-2-yl acetate, as well as pharmaceutically acceptable salts of prasugrel, as well as polymorphs, solvates, hydrates, dehydrates, co-crystals, anhydrous, and amorphous forms thereof. Prasugrel contains a chiral atom, and thus, as used herein, "prasugrel" refers to the levorotatory enantiomer, dextrorotatory enantiomer, racemic mixtures of these enantiomers, and combinations thereof. The invention thus encompasses pharmaceutical compositions and dosage forms comprising pharmaceutically acceptable salts of prasugrel, and polymorphs, solvates, hydrates, dehydrates, co-crystals, anhydrous, and amorphous forms of prasugrel in combination with a cyclodextrin derivative.

As used herein, "pharmaceutically acceptable" refers to those excipients, compounds, addition salts, materials, and/or compositions which are, within the scope of sound medical judgment, suitable for contact with the tissues of human beings and animals without excessive toxicity, irritation, allergic response, or other possible complications commensurate with a reasonable benefit/risk ratio.

Cyclodextrin Derivatives

The compositions, formulations and/or unit dosage forms of the present invention comprise a cyclodextrin derivative. As used herein, "cyclodextrin derivative" refers to a cyclic oligosaccharide comprising five or more α-D-glucopyranoside units linked in a circular 1→4 configuration, and comprising a substituent group attached to one or more of the glucopyranoside units at the 2, 3 and/or 6 position(s) through an ether bond (—O—R—, where R refers to the substituent group).

Cyclodextrin derivatives for use with the present invention are compounds of formula I:

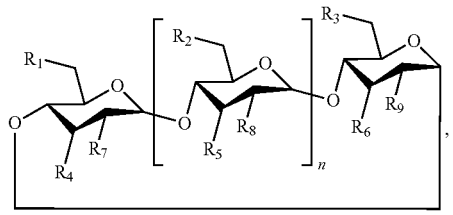

wherein n is 4, 5 or 6, wherein $R_1$, $R_2$, $R_3$, $R_4$, $R_5$, $R_6$, $R_7$, $R_8$ and $R_9$ are independently selected from: —OH, a straight-chain or branched —O—($C_1$-$C_8$-(alkylene))-$SO_3^-$ group, an optionally substituted straight-chain, branched, or cyclic —O—($C_1$-$C_{10}$) group, an optionally substituted straight-chain, branched, or cyclic —S—($C_1$-$C_{10}$) group, and a saccharide.

In some embodiments, a cyclodextrin for use with the present invention is selected based upon an average degree of substitution ("ADS"), which as used herein refers to the average number of substituent groups per cyclodextrin molecule. The average degree of substitution for cyclodextrin derivatives is described in detail in WO 2009/018069, which is incorporated herein by reference in its entirety. As used herein, a cyclodextrin derivative composition for use with the present invention is referred to by the following notation: the substituent(s) are abbreviated (e.g., sulfobutyl ether groups are abbreviated as "SBE") with a subscript denoting the ADS of the substituent, and cyclodextrin structure is defined. For example, a sulfobutyl ether-derivatized β-cyclodextrin composition having an ADS of 6.5 is referred to as "$SBE_{6.5}$-β-CD." As a second example, a β-cyclodextrin composition comprising cyclodextrin molecules derivatized with both sulfobutyl ether and hydroxypropyl groups is referred to as "$SBE_{4.2}$-$HP_{2.5}$-β-CD," wherein the ADS of the sulfobutyl ether groups is 4.2 and the ADS of the hydroxypropyl groups is 2.5.

In some embodiments, at least one of $R_1$, $R_2$, $R_3$, $R_4$, $R_5$, $R_6$, $R_7$, $R_8$ and $R_9$ is substituted with a straight-chain —O—($C_4$-(alkylene))-$SO_3^-$ group. Exemplary —O—($C_1$-$C_8$-(alkylene))-$SO_3^-$ groups suitable for use with the present invention include, but are not limited to, sulfoethyl ether, sulfopropyl ether, 1-methyl-sulfopropyl ether, sulfobutyl ether, 1-methyl-sulfobutyl ether, 2-methyl-sulfobutyl ether, 1-methyl-sulfobut-3-yl ether, 2-ethyl-sulfobutyl ether, 3-ethyl-sulfobutyl ether, sulfopentyl ether, 1-sulfopent-3-yl ether, sulfohexyl ether, sulfoheptyl ether, sulfooctyl ether, and the like, and combinations thereof.

In some embodiments, $R_1$, $R_2$, $R_3$, $R_4$, $R_5$, $R_6$, $R_7$, $R_8$ and $R_9$ are independently a straight-chain or branched —O—($C_1$-$C_8$-(alkylene))-$SO_3^-$ group having an ADS of about 4 to about 8, about 4 to about 7.5, about 4 to about 7, about 4 to about 6.5, about 4.5 to about 8, about 4.5 to about 7.5, about 4.5 to about 7, about 5 to about 8, about 5 to about 7.5, about 5 to about 7, about 5.5 to about 8, about 5.5 to about 7.5, about 5.5 to about 7, about 5.5 to about 6.5, about 6 to about 8, about 6 about 7.5, about 6 to about 7.1, about 6.5 to about 8, or about 6.5 to about 7.5 per cyclodextrin derivative, and the remaining substituents are —H.

In some embodiments, a substituent is an optionally substituted straight-chain, branched, or cyclic —O—($C_1$-$C_{10}$) group. In some embodiments, a substituent is an optionally substituted straight-chain, branched, or cyclic —O—($C_1$-$C_8$) group, an optionally substituted straight-chain, branched, or cyclic —O—($C_2$-$C_6$) group, or an optionally substituted straight-chain, branched, or cyclic —O—($C_3$-$C_5$) group.

As used herein, "optionally substituted" refers to one or more optional substituents selected from: halogen (i.e., —F, —Cl, —Br, —I), —$NO_2$, —C≡N, —$OR_{22}$, —$SR_{22}$, —$SO_2R_{22}$, —C(=O)$OR_{22}$, —C(=O)$R_{22}$, —C(=O)N($R_{22}$)$_2$, —$SO_2$N($R_{22}$)$_2$, —$SO_2$N(H)C(=O)$R_{22}$, —$SO_2$N(H)C(=O)$OR_{22}$ (wherein $R_{22}$ is not H), —N($R_{22}$)$_2$, —N($R_{22}$)$SO_2R_{22}$, —N($R_{22}$)C(O)$_mR_{22}$ (wherein m=1 or 2), —N($R_{22}$)C(O)N($R_{22}$)$_2$, —N($R_{22}$)$SO_2$N($R_{22}$)$_2$, —O—C(=O)$R_{22}$, —O—C(=O)$OR_{22}$, —O—C(=O)N($R_{22}$)$_2$, —C(=O)N(H)$SO_2$N($R_{22}$)$_2$, —C(=O)N(H)$SO_2R_{22}$, oxo (or keto, i.e., =O), thioxo (i.e., =S), imino (i.e., =$NR_{22}$), —$NR_{22}$—C(=$NR_{22}$)$R_{22}$, —$NR_{22}$—C(=$NR_{22}$)N($R_{22}$)$_2$, —C(=$NR_{22}$)N($R_{22}$)$_2$, —O—C(=$NR_{22}$)N($R_{22}$)$_2$, —O—C(=$NR_{22}$)$R_{22}$, —C(=$NR_{22}$)$R_{22}$, —C(=$NR_{22}$)$OR_{22}$, and ionic forms thereof (e.g., —$N^+$($R_{22}$)$_2X^-$, and the like, wherein X— is a pharmaceutically acceptable anion), wherein $R_{22}$ is independently selected at each occurrence from H, and $C_1$-$C_4$ alkyl.

Exemplary optionally substituted straight-chain or branched —O—($C_1$-$C_{10}$) groups include, but are not limited to, 2-hydroxypropyl ether, 3-hydroxypropyl ether, 2,3-dihydroxypropyl ether, 3-oxobutyl ether, and 2-ethoxy-ethyl ether.

In some embodiments, at least one of $R_1$, $R_2$, $R_3$, $R_4$, $R_5$, $R_6$, $R_7$, $R_8$ and $R_9$ is a —O-(hydroxy-substituted-$C_3$) group. In some embodiments, the cyclodextrin derivative comprises β-cyclodextrin that includes a —O-(hydroxy-substituted-$C_3$) group having an ADS of about 1 to about 8, about 2 to about 8, about 3 to about 7, about 4 to about 7.5, about 4.3 to about 7.5, about 1, about 2, about 2.5, about 3, about 3.5, about 4, about 4.3, about 5, about 5.5, about 6, about 6.5, about 7, or about 7.5.

In some embodiments, at least one of $R_1$, $R_2$, $R_3$, $R_4$, $R_5$, $R_6$, $R_7$, $R_8$ and $R_9$ is an optionally substituted straight-chain, branched, or cyclic —S—($C_1$-$C_{10}$) group. For example, cyclodextrins suitable for use with the present invention include β- and γ-cyclodextrin optionally substituted with one or more carboxy-substituted alkylthioether groups. Representative structures include sugammadex, a γ-cyclodextrin substituted with 8 carboxypropyl thioether groups (i.e., CAS Reg. No. 343306-79-6, available as BRIDION®, N.V. Organon, Oss, NL).

In some embodiments, $R_1$, $R_2$, $R_3$, $R_4$, $R_5$, $R_6$, $R_7$, $R_8$ and $R_9$ are independently a saccharide. As used herein, a "saccharide" refers to naturally occurring and synthetic monosaccharides, disaccharides, trisaccharides, tetrasaccharide, and pentasaccharides, as well as sugar alcohols and polyols that are approved as generally recognized as safe for human consumption by the U.S. Food and Drug Administration, wherein the saccharide is covalently bound to the cyclodextrin through a hydroxy group present on the cyclodextrin.

Monosaccharides suitable for use with the present invention include, but are not limited to, allose, altrose, arabinose, erythrose, erythrulose, fructose, galactose, glucose, glyceraldehyde, idose, lyxose, psicose, ribose, ribulose, sorbose, tagatose, talose, threose, xylose, xylulose, and the like, and combinations thereof.

Disaccharides suitable for use with the present invention include, but are not limited to, cellobiose, lactose, maltose, sucrose, trehalose, turanose, and the like, and combinations thereof.

Trisaccharides suitable for use with the present invention include, but are not limited to, raffinose, melezitose, maltotriose, and the like, as well as nigerotrioses, gentiotrioses, and the like, comprising any combination of the above-listed monosaccharides.

Tetrasaccharides suitable for use with the present invention include, but are not limited to, acarbose, nystose, stachyose, and the like, as well as nigerotetraoses, gentiotetraoses, and the like, comprising any combination of the above-listed monosaccharides.

Pentasaccharides suitable for use with the present invention include, but are not limited to, nigeropentaoses, gentiopentaoses, and the like, comprising any combination of the above-listed monosaccharides.

The di-, tri-, tetra-, and pentasaccharides for use with the present invention include malto-oligosaccharides (i.e., oligomers that include only α-1,4 glucosidic linkages), isomalto-oligosaccharides (i.e., "branched" oligomers that include both α-1,4 and α-1,6 glucosidic linkages), nigero-oligosaccharides (i.e., α-1,3 linked oligomers), gentio-oligosaccharides (i.e., β-1,6 linked oligomers), Sugar alcohols suitable for use with the present invention include, but are not limited to, arabitol, erythritol, glycerol, lactitol, maltitol, mannitol, sorbitol, xylitol, and the like, and combinations thereof.

Polyols suitable for use with the present invention include, but are not limited to, inositol, and the like.

In some embodiments, a cyclodextrin derivative is a maltosyl-β-cyclodextrin in which one of the primary hydroxyl groups of β-cyclodextrin is substituted by maltose through the α-1,6 glycosidic linkage.

Exemplary cyclodextrin compositions, and methods of making the same, that are suitable for use with the present invention also include those described in U.S. Pat. Nos. 5,134,127, 5,241,059, 5,376,645, 5,874,418, 6,046,177, 6,133,248; 6,153,746, 6,204,256, 7,034,013, U.S. Patent Pub. No. 2009/0012042, WO 2005/117911, and U.S. application Ser. Nos. 12/363,719 and 12/404,174, the contents of each of which are incorporated herein by reference in the entirety.

In some embodiments, the cyclodextrin derivative is a compound of formula II:

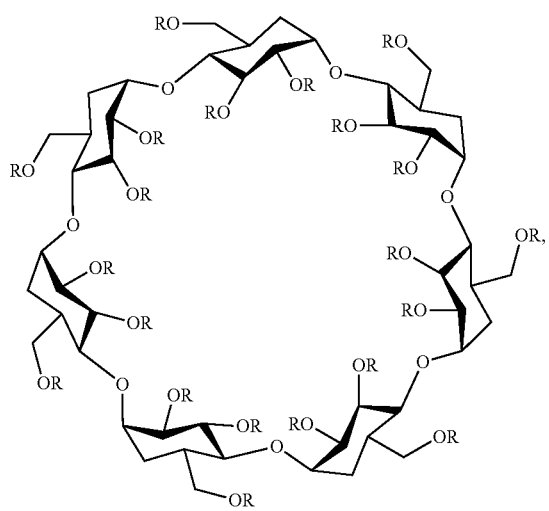

II wherein R=(H)$_{21-x}$ or (—(CH$_2$)$_4$—SO$_3^-$Na$^+$)$_x$. In some embodiments, x=6.0-7.1. In some embodiments, the cyclodextrin derivative of formula II has an average molecular weight of about 2163 g/mol.

In some embodiments, the cyclodextrin derivative is a sulfobutyl ether-β-cyclodextrin having an ADS of about 6.5 (e.g., CAPTISOL®, CyDex Pharmaceuticals, Inc., Lenexa, Kans.). CAPTISOL® cyclodextrin is a polyanionic β-cyclodextrin derivative with a sodium sulfonate salt separated from the lipophilic cyclodextrin cavity by a butyl ether spacer group, or sulfobutylether (SBE). CAPTISOL® cyclodextrin has been shown to be safe when administered parenterally, orally, or via inhalation and does not exhibit the nephrotoxicity associated with β-cyclodextrin. Relative to β-cyclodextrin, CAPTISOL® sulfoalkyl ether cyclodextrin provides comparable or higher complexation characteristics and superior water solubility in excess of 90 g per 100 mL, a 50-fold improvement.

In some embodiments, the cyclodextrin derivative includes a substituent that bears an ionic group that can optionally form a salt with a pharmaceutically acceptable anion or cation. Pharmaceutically acceptable cations suitable for forming salts with negatively charged cyclodextrin derivatives of the present invention include, but are not limited to, H$^+$, Li$^+$, Na$^+$, K⁺, Mg²⁺, Ca²⁺, ammonium and amine cations such as cations of $(C_1-C_6)$-alkylamines, $(C_4-C_8)$-cycloalkylamines (e.g., piperidine, pyrazine, and the like), $(C_1-C_6)$-alkanolamines, and $(C_4-C_8)$-cycloalkanolamines, and the like, and combinations thereof. Pharmaceutically acceptable anions suitable for forming salts with positively charged cyclodextrin derivatives of the present invention include, but are not limited to, halides (e.g., Cl⁻ and the like), anions of $(C_1-C_6)$-alkyl acids (e.g., acetate, oxalate, fumarate, succinate, and the like, and combinations thereof.

Pharmaceutical Compositions and Unit Dosage Forms

The present invention is directed to pharmaceutical compositions and unit dosage forms comprising prasugrel and a cyclodextrin derivative. The pharmaceutical compositions of the present invention are suitable for oral and/or parenteral administration to a subject. Parenteral administration of the pharmaceutical compositions can include, but is not limited to, intravenous (including bolus injection), intraarterial, intramuscular, transmucosal (e.g., nasal, rectal, and the like), and subcutaneous administration. Because parenteral administration of compositions of the present invention typically bypasses the subject's natural defenses against contaminants, the pharmaceutical compositions can be sterile or capable of being sterilized prior to administration.

Exemplary pharmaceutical compositions include, but are not limited to, solutions, suspensions or emulsions ready for administration, solutions, suspensions or emulsions ready to be dissolved or suspended in a pharmaceutically acceptable vehicle, and dry products ready to be dissolved or suspended in a pharmaceutically acceptable vehicle.

Generally, the pharmaceutical compositions of the present invention comprise prasugrel in a concentration suitable for treating a condition amenable to treatment with prasugrel. Thus, the pharmaceutical compositions of the present invention can be used to prepare a unit dosage form comprising a therapeutically effective amount of prasugrel for administering to a subject in need thereof. In some embodiments, a unit dosage form can comprise pharmaceutical compositions comprising a concentration of prasugrel that is suitable for administration without dilution.

Sterile solutions, suspensions, emulsions and the like can be prepared by incorporating prasugrel into an appropriate solvent or carrier with the other optional ingredients enumerated herein, followed by sterilization. Sterile powders can be prepared by spray drying, aseptic spray drying, vacuum drying, or freeze drying a sterile solution, suspension, or emulsion to provide a dried solid (e.g., a powder) comprising prasugrel along with any additional excipients.

In some embodiments, a pharmaceutical composition or unit dosage form of the present invention comprises a stock solution that is diluted with a liquid carrier or diluent prior to administration to a subject. Thus, the pharmaceutical compositions and unit dosage forms of the present invention include sterile aqueous solutions, suspensions and dispersions, as well as sterile solids (e.g., powders) comprising prasugrel that can be extemporaneously diluted or solubilized to provide a sterile solution, suspension or dispersion.

In some embodiments, prasugrel is present in a pharmaceutical composition or unit dosage form of the present invention in a concentration of about 0.001 mg/mL to about 1 mg/mL, about 0.005 mg/mL to about 1 mg/mL, about 0.01 mg/mL to about 1 mg/mL, about 0.05 mg/mL to about 1 mg/mL, about 0.1 mg/mL to about 1 mg/mL, about 0.5 mg/mL to about 1 mg/mL, about 0.001 mg/mL to about 0.5 mg/mL, about 0.005 mg/mL to about 0.5 mg/mL, about 0.01 mg/mL to about 0.5 mg/mL, about 0.05 mg/mL to about 0.5 mg/mL, about 0.1 mg/mL to about 0.5 mg/mL, about 0.001 mg/mL to about 0.1 mg/mL, about 0.005 mg/mL to about 0.1 mg/mL, about 0.01 mg/mL to about 0.1 mg/mL, or about 0.05 mg/mL to about 0.1 mg/mL.

In some embodiments, the cyclodextrin derivative is present in a pharmaceutical composition or unit dosage form of the present invention in a concentration of about 0.1 mg/mL to about 1000 mg/mL, about 0.1 mg/mL to about 700 mg/mL, about 0.1 mg/mL to about 500 mg/mL, about 0.1 mg/mL to about 250 mg/mL, about 0.1 mg/mL to about 200 mg/mL, about 0.1 mg/mL to about 150 mg/mL, about 0.1 mg/mL to about 100 mg/mL, about 0.1 mg/mL to about 50 mg/mL, about 1 mg/mL to about 1000 mg/mL, about 1 mg/mL to about 700 mg/mL, about 1 mg/mL to about 500 mg/mL, about 1 mg/mL to about 250 mg/mL, about 1 mg/mL to about 200 mg/mL, about 1 mg/mL to about 150 mg/mL, about 1 mg/mL to about 100 mg/mL, about 1 mg/mL to about 50 mg/mL, about 10 mg/mL to about 1000 mg/mL, about 10 mg/mL to about 700 mg/mL, about 10 mg/mL to about 500 mg/mL, about 10 mg/mL to about 250 mg/mL, about 10 mg/mL to about 200 mg/mL, about 10 mg/mL to about 150 mg/mL, about 10 mg/mL to about 100 mg/mL, about 10 mg/mL to about 50 mg/mL, about 50 mg/mL to about 1000 mg/mL, about 50 mg/mL to about 700 mg/mL, about 50 mg/mL to about 500 mg/mL, about 50 mg/mL to about 250 mg/mL, about 50 mg/mL to about 200 mg/mL, about 50 mg/mL to about 150 mg/mL, about 50 mg/mL to about 100 mg/mL, about 100 mg/mL to about 1000 mg/mL, about 100 mg/mL to about 700 mg/mL, about 100 mg/mL to about 500 mg/mL, about 100 mg/mL to about 250 mg/mL, about 200 mg/mL to about 1000 mg/mL, about 200 mg/mL to about 700 mg/mL, about 200 mg/mL to about 500 mg/mL, about 200 mg/mL to about 250 mg/mL, about 500 mg/mL to about 1000 mg/mL, or about 500 mg/mL to about 700 mg/mL.

In some embodiments, the present invention is directed to a pharmaceutical composition comprising prasugrel and a cyclodextrin derivative of formula I:

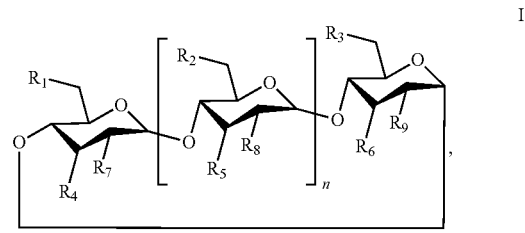

wherein n is 4, 5 or 6, wherein $R_1$, $R_2$, $R_3$, $R_4$, $R_5$, $R_6$, $R_7$, $R_8$ and $R_9$ are independently selected from: —OH, a straight-chain or branched —O—$(C_1-C_8$-(alkylene))-$SO_3^-$ group, an optionally substituted straight-chain, branched, or cyclic —O—$(C_1-C_{10})$ group, an optionally substituted straight-chain, branched, or cyclic —S—$(C_1-C_{10})$ group, and a saccharide, and wherein the cyclodextrin derivative is present in a concentration of at least 100:1 by weight relative to the prasugrel.

In some embodiments, the cyclodextrin derivative is present in a pharmaceutical composition or unit dosage form of the present invention in a concentration of at least 100:1 by weight, at least 125:1 by weight, at least 150:1 by weight, at least 200:1 by weight, at least 250:1 by weight, at least 300:1 by weight, at least 400:1 by weight, at least 500:1 by weight, at least 600:1 by weight, at least 700:1 by weight, at least 800:1 by weight, at least 900:1 by weight, or at least 1000:1 by weight relative to the prasugrel.

In some embodiments, the cyclodextrin derivative is present in a pharmaceutical composition or unit dosage form of the present invention in a concentration of about 100:1 to about 8000:1 by weight, about 100:1 to about 5000 by weight, about 100:1 to about 1000:1 by weight, about 100:1 to about 900:1 by weight, about 100:1 to about 700:1 by weight, about 100:1 to about 600:1 by weight, about 100:1 to about 500:1 by weight, about 100:1 to about 400:1 by weight, about 100:1 to about 300:1 by weight, about 100:1 to about 250:1 by weight, about 100:1 to about 200:1 by weight, about 100:1 to about 175:1 by weight, about 100:1 to about 150:1 by weight, about 100:1 to about 125:1 by weight, about 125:1 to about 700:1 by weight, about 125:1 to about 500:1 by weight, about 125:1 to about 250:1 by weight, about 150:1 to about 700:1 by weight, about 150:1 to about 500:1 by weight, about 150:1 to about 300:1 by weight, about 175:1 to about 700:1 by weight, about 175:1 to about 500:1 by weight, about 150:1 to about 300:1 by weight, about 200:1 to about 700:1 by weight, about 200:1 to about 500:1 by weight, about 250:1 to about 700:1 by weight, about 250:1 to about 500:1 by weight, about 300:1 to about 700:1 by weight, about 300:1 to about 500:1 by weight, about 700:1 to about 8000:1 by weight, about 700:1 to about 5000:1 by weight, about 700:1 to about 1000:1 by weight, about 700:1 to about 900:1 by weight, or about 700:1 to about 800:1 by weight of the prasugrel.

In some embodiments, the cyclodextrin derivative is present in a pharmaceutical composition or unit dosage form of the present invention in a concentration of at least 50:1 by mole, at least 75:1 by mole, at least 100:1 by mole, at least 125:1 by mole, at least 150:1 by mole, at least 200:1 by mole, or at least 250:1 by mole relative to the prasugrel.

In some embodiments, the cyclodextrin derivative is present in a pharmaceutical composition or unit dosage form of the present invention in a concentration of about 50:1 to about 300:1 by mole, about 50:1 to about 250:1 by mole, about 50:1 to about 200:1 by mole, about 50:1 to about 150:1 by mole, about 50:1 to about 125:1 by mole, about 50:1 to about 100:1 by mole, about 50:1 to about 75:1 by mole, about 75:1 to about 300:1 by mole, about 75:1 to about 250:1 by mole, about 75:1 to about 200:1 by mole, about 75:1 to about 150:1 by mole, about 75:1 to about 125:1 by mole, about 75:1 to about 100:1 by mole, about 100:1 to about 300:1 by mole, about 100:1 to about 250:1 by mole, about 100:1 to about 200:1 by mole, about 100:1 to about 150:1 by mole, about 100:1 to about 125:1 by mole, about 150:1 to about 300:1 by mole, about 200:1 to about 300:1 by mole, or about 250:1 to about 300:1 by mole relative to prasugrel.

In some embodiments, the pharmaceutical compositions and unit dosage forms of the present invention are substantially homogeneous. As used herein, "homogeneous" refers to mixtures, solutions, suspensions, compositions, dosage forms, and/or formulations of the present invention that have a uniform distribution of ingredients throughout. Homogeneity is synonymous with uniformity and can refer to intra-sample uniformity, batch-to-batch uniformity, run-to-run uniformity, and/or dosage form-to-dosage form uniformity. For example, intra-sample uniformity can be determined by analyzing a first portion of a sample, mixture, or composition and comparing this with a second portion of the same sample, mixture, or composition. Typical deviations of a composition (e.g., variation in the percentage by weight of excipients and the like) of a substantially homogeneous composition are 5% or less, 3% or less, 2% or less, 1% or less, or within experimental error.

In some embodiments, a pharmaceutical composition or unit dosage form of the present invention comprises a pharmaceutically acceptable excipient. As used herein, the term "excipient" refers to any inert substance that can be combined with prasugrel and the sulfoalkyl ether cyclodextrin for preparing the pharmaceutical compositions.

Pharmaceutically acceptable excipients suitable for use with the present invention include, but are not limited to, a carrier, a preservative, an antioxidant, an acidifying agent, an alkalinizing agent, a buffering agent, a bulking agent, a complexation enhancing agent, a cryoprotectant, a density modifier, an electrolyte, a flavor, a fragrance, a lyophilizing aid (e.g., a bulking agent and/or stabilizing agent), a plasticizer, a solubility-enhancing agent, a stabilizing agent, a sweetener, a surface tension modifier, a volatility modifier, a viscosity modifier, and combinations thereof. In addition, one of skill in the art will recognize that pharmaceutically acceptable excipients can be used in the present invention including those listed in *The Handbook of Pharmaceutical Excipients,* 5th Ed., The Pharmaceutical Press and American Pharmacists Association, London, UK and Washington, D.C. (2006), which is incorporated herein by reference in its entirety.

In some embodiments, a pharmaceutical composition or unit dosage form of the present invention comprises a pharmaceutically acceptable carrier. As used herein, a "carrier" refers to vehicle suitable for transferring and/or diluting a pharmaceutical composition or unit dosage form of the present invention. Pharmaceutically acceptable carriers suitable for use with the present inventions include, but are not limited to, liquids, solids, colloids, gels, and combinations thereof. Liquid carriers suitable for use with the present, invention include solvents, liquid dispersion mediums, and the like, such as, but not limited to, water, ethanol, a polyol (e.g., glycerol, propylene glycol, liquid polyethylene glycols, and the like), a vegetable oil, a nontoxic glyceryl ester, and combinations thereof. In some embodiments, a liquid carrier is selected from: a dextrose solution, a saline solution, plasma, and lactated Ringer's solution.

In some embodiments, the pH of a pharmaceutical composition or unit dosage form is controlled. In some embodiments, a pharmaceutical composition or unit dosage form of the present invention comprises a pharmaceutically acceptable buffer and/or pH adjusting agent (e.g., an acidifying agent and/or alkalinizing agent). In some embodiments, a pharmaceutical composition or unit dosage form of the present invention has a pH of about 2 to about 9, about 2 to about 8, about 2 to about 7, about 2 to about 6, about 2 to about 4, about 3 to about 9, about 3 to about 8, about 3 to about 7, about 3 to about 6, about 4 to about 9, about 4 to about 8, about 4 to about 7, about 4 to about 6, about 6 to about 9, about 6 to about 8, about 3, about 4, about 5, about 6, about 7, or about 8.

In some embodiments, a pharmaceutical composition or unit dosage form that is to be diluted prior to administration to a subject has a pH of about 2 to about 9, about 2 to about 7, about 2 to about 6, about 2 to about 5, or about 2 to about 4. In some embodiments, after dilution (e.g., with an liquid carrier) a unit dosage form of the present invention has a pH of about 4 to about 9, about 4 to about 8, about 4 to about 7, about 4 to about 6, about 5 to about 9, or about 6 to about 8 at the time of administration to a subject in need thereof.

In some embodiments, a pharmaceutical composition or unit dosage form of the present invention comprises a buffer. In some embodiments, a buffer is present in a concentration of about 0.01 M to about 10 M, about 0.02 M to about 5 M, about 0.03 M to about 2 M, about 0.05 M to about 1 M, about 0.1 M to about 0.5 M, about 0.05 M, about 0.1 M, about 0.15 M, about 0.2 M, about 0.25 M, or about 0.3 M.

Buffers suitable for use with the present invention include, but are not limited to, an acetate buffer, a citrate buffer, a phosphate buffer, a borate buffer, a carbonate buffer, a tris(hydroxymethyl)aminomethane buffer, a hydroxide buffer, and the like, and combinations thereof.

Because the solubility of prasugrel in aqueous solution is pH-dependent, the concentration of the cyclodextrin derivative in a pharmaceutical composition or unit dosage form of the present invention can vary with pH. Generally, as the pH of the pharmaceutical composition is decreased, a lower concentration of a cyclodextrin derivative can be required to solubilize the prasugrel. Thus, in some embodiments a pharmaceutical composition or unit dosage form of the present invention has a pH of about 4 or less, or about 2 to about 4, and the ratio of the cyclodextrin derivative to prasugrel is at least 100:1 by weight, or about 100:1 to about 700:1 by weight, or any other weight ratio there between that is disclosed herein. In some embodiments, a pharmaceutical composition or unit dosage form of the present invention has a pH of about 4 or greater, or a pH of about 4 to about 9, and the ratio of the cyclodextrin to prasugrel is at least 700:1 by weight, or about 700:1 to about 1000:1 by weight, or any other weight ratio there between that is disclosed herein.

In some embodiments, a pharmaceutical composition or unit dosage form of the present invention comprises a second therapeutic having anti-thrombotic, anti-platelet aggregation, antiatheroaclerotic, antirestenotic and/or anti-coagulant activity. Such drugs are useful in treating thrombosis-related diseases including thrombosis, atherosclerosis, restenosis, hypertension, angina pectoris, arrhythmia, heart failure, myocardial infarction, glomerulonephritis, thrombotic and thromboembolic stroke, peripheral vascular diseases, other cardiovascular diseases, cerebral ischemia, inflammatory disorders and cancer, as well as other disorders in which thrombin and its receptor play a pathological role.

Suitable second therapeutic agents include, but are not limited to, an analog or derivative of, a nonsteroidal antiinflammatory drug, a selective factor Xa inhibitor, a direct thrombin inhibitor, a prostaglandin analog, an adenosine diphosphate (ADP) inhibitor, a platelet aggregation inhibitor, an antiplatelet agent, a glycoprotein inhibitor or antagonist, an antisickling agent, a hemorrheologic agent, a thrombolytic agent, a thrombolytic enzyme, a thromboxane A2 biosynthesis inhibitors, a thromboxane antagonist, a cyclooxygenase inhibitor, an angiotensin antagonist, an endothelin antagonist, a phosphodiesterase inhibitor, an angiotensin converting enzyme (ACE) inhibitors, a neutral endopeptidase inhibitors, an anticoagulants, a diuretic, a tissue plasminogen activator, a modified tissue plasminogen activator, a biologic response modifier, a statin, a calcium channel blocking agent, an antiarrhythmic agent, an α-adrenergic agonist, a β-adrenergic antagonist, and combinations thereof.

In some embodiments, a pharmaceutical composition or unit dosage form of the present invention comprises a second therapeutic agent such as, but not limited to, diclofenac, droxicam, etolodac, fenoprofen, flurbiprofen, indomethacin, isoxicam, ketoprofen, lornoxicam, meloxicam, mefenamate, naproxen, oxaprozin, piroxicam, sulindac, tenoxicam, apixaban, otamixaban, rivaroxaban, eptifibatide, beraprost, prostacyclin, iloprost, treprostinil, an analog or derivative of prasugrel, clopidogrel, ticagrelor, ticlopidine, abciximab, cloricromen, ditazole, indobufen, picotamide, sulfinpyrazone, abciximab, eptifibatide, tirofiban, cetiedil, alteplase, anistreplase, brinase, drotrecogin alfa, monteplase, reteplase, saruplase, streptokinase, tenecteplase, urokinase, fibrinolysin, ancrod, aspirin, picotamide, ramatroban, seratrodast, aloxiprin, carbasalate calcium, celecoxib, ibuprofen, rofecoxib, candesartan, eprosartan, irbesartan, losartan, olmesartan, telmisartan, valsartan, ambrisentan, atrasentan, bosentan, sitaxentan, tezosentan, cilostazol, dipyridamole, enoximone, milrinone, captopril, enalapril, enaliprilat, spirapril, quinapril, perindopril, ramipril, fosinopril, trandolapril, lisinopril, moexipril, benazapril, candoxatril, ecadotril, candoxatril, ecadotril, unfractionated heparin, ardeparin, bemiparin, certoparin, dalteparin, enoxaparin, fondaparin, fragmin, melagatran, nadroparin, parnaparin, reviparin, tinzaparin, argatroban, dabigatran, melagatran, ximelagatran, defibrotide, ramatroban, antithrombin III, fondaparinux, idraparinux, danaparoid, sulodexide, dermatan sulfate, a synthetic pentasaccharide, a hirudin, disulfatohirudin bivalirudin, desirudin, lepirudin, acenocoumarol, coumatetralyl, dicoumarol, ethyl biscoumacetate, phenprocoumon, clorindione, diphenadione, phenindione, tioclomarol, warfarin, chlorothiazide, hydrochlorothiazide, ethacrynic acid, furosemide, amiloride, chlorothiazide, hydrochlorothiazide, atorvastatin, fluvastatin, lovastatin, pravastatin, pravastatin, rosuvastatin, simvastatin, amlodipine, felodipine, diltiazem, nifedipine, nicardipine, nisoldipine, bepridil, verapamil, dofetilide, ibutilide, metoprolol, propranolol, atenolol, betaxolol, bisoprolol, carvediol, nadolol, nebivolol, timolol, ajmaline, disopyramide, prajmaline, procainamide, quinidine, sparteine, aprindine, lidocaine, mexiletine, tocainide, encainide, flecainide, lorcainide, moricizine, propafenone, acebutolol, pindolol, amiodarone, bretylium, bunaftine, dofetilide, sotalol, adenosine, atropine, digoxin, doxazosin, terazosin, prazosin, and combinations thereof.

As used herein, a "unit dosage form" refers to a composition containing a specific amount of prasugrel, the whole of which is intended to be administered to a subject in a single dose. A unit dosage form can be distinguished from a supply of a multi-dose amount of a pharmaceutical composition, e.g., a bottle of medicine, from which a unit dose is measured out.

In some embodiments, a unit dosage form of the present invention comprises a therapeutically effective amount of prasugrel. As used herein, a "therapeutically effective amount" refers to an amount of prasugrel that elicits a biological or medicinal response in a tissue, system, animal or human that is being sought by a researcher, veterinarian, medical doctor or other clinician, which includes alleviation of the symptoms of a disease or disorder being treated.

A unit dosage form typically comprises the pharmaceutical composition of the present invention and optionally, one or more pharmaceutically acceptable excipients, wherein the amount of prasugrel present in the unit dosage form is sufficient for a single administration to a subject in need thereof. Unit dosage forms of the present invention include, but are not limited to, liquid solutions, liquid suspensions, liquid dispersions, emulsions, gels, powders, tablets, capsules, caplets, and the like. Treatment of a disease or condition amenable to treatment with prasugrel can comprises periodic administration of a unit dosage form of the present invention, for example, once per day, twice per day, thrice per day, four times per day, with one or more meals, at least an hour before or two hours after one or more meals, every four to six hours, every eight hours, every twelve hours, or some other interval.

In some embodiments, a unit dosage form of the present invention comprises 1 mg to 120 mg prasugrel. In some embodiments, a unit dosage form of the present invention comprises a maintenance dose of prasugrel. As used herein, a "maintenance dose" refers to an amount of prasugrel that can be administered on a periodic manner (e.g., once daily, twice daily, and the like) to maintain an in vivo concentration of prasugrel or an active metabolite thereof in a subject suffering from a disease or disorder amenable to treatment with prasugrel. In some embodiments, a unit dosage form of the present invention comprises about 1 mg to about 20 mg, about 1 mg to about 10 mg, about 1 mg to about 8 mg, about 1 mg to about 6 mg, about 1 mg to about 5 mg, about 1 mg to about 2.5 mg, about 1 mg to about 2 mg, about 2 mg to about 20 mg, about 2 mg to about 10 mg, about 2 mg to about 8 mg, about 2 mg to about 6 mg, about 2 mg to about 5 mg, about 5 mg to about 20 mg, about 5 mg to about 10 mg, about 10 mg to about 20 mg, about 20 mg, about 15 mg, 10 mg, about 8 mg, about 7.5 mg, about 6 mg, about 5 mg, about 4 mg, about 2.5 mg, or about 2 mg prasugrel.

In some embodiments, a unit dosage form of the present invention comprises a loading dose of prasugrel. As used herein, a "loading dose" refers to an initial higher dose of prasugrel that is administered at the beginning of a course of treatment before a lower maintenance dose is started. In some embodiments, a unit dosage form of the present invention comprises about 20 mg to about 120 mg, about 20 mg to about 100 mg, about 20 mg to about 80 mg, about 20 mg to about 60 mg, about 20 mg to about 50 mg, about 40 mg to about 120 mg, about 40 mg to about 100 mg, about 40 mg to about 80 mg, about 40 mg to about 60 mg, about 50 mg to about 120 mg, about 50 mg to about 100 mg, about 50 mg to about 80 mg, about 50 mg to about 70 mg, about 60 mg to about 120 mg, about 60 mg to about 100 mg, about 60 mg to about 80 mg, about 80 mg to about 120 mg, about 80 mg to about 100 mg, about 120 mg, about 100 mg, about 80 mg, about 70 mg, about 60 mg, about 50 mg, about 40 mg, or about 20 mg prasugrel.

In some embodiments, a unit dosage form of the present invention is a solid. In some embodiments, a solid unit dosage form of the present invention is a lyophilized solid or an aseptic spray-dried solid. In some embodiments, a dosage form of the present invention is suitable for dilution and/or reconstitution with a predetermined amount of a liquid carrier. For example, a unit dosage form (e.g., a liquid or a solid) of the present invention can be diluted with about 10 mL to about 500 mL, about 10 mL to about 250 mL, about 10 mL to about 100 mL, or about 10 mL to about 50 mL of a liquid carrier.

In some embodiments, a unit dosage form of the present invention comprises prasugrel in a concentration of about 0.005% to about 2% w/v, a cyclodextrin derivative in a concentration of about 5% to about 40% w/v, and the unit dosage form is an aqueous solution having a pH of about 2 to about 4. In some embodiments, a unit dosage form of the present invention comprises prasugrel in a concentration of about 0.005% to about 1% w/v, a cyclodextrin derivative in a concentration of about 5% to about 40% w/v, and the unit dosage form is an aqueous solution having a pH of about 4 to about 9.

The pharmaceutical compositions and unit dosage forms of the present invention are stable. Thus, in those embodiments in which a solid or liquid unit dosage form is diluted, the diluting can be performed immediately prior to administering, or sometime before the administering without any significant loss of therapeutic efficacy.

In some embodiments, prasugrel in a liquid pharmaceutical composition or unit dosage form of the present invention having a pH of about 2 to about 4 degrades by 10% or less over a period of 24 hours, or 15% or less over a period of 48 hours.

In some embodiments, prasugrel in a liquid pharmaceutical composition or unit dosage form of the present invention having a pH of about 4 to about 9 degrades by 20% or less over a period of 24 hours, or 40% or less over a period of 48 hours.

Thus, a liquid pharmaceutical composition or liquid unit dosage form of the present invention can be prepared at least 24 hours, or about 48 hours in advance of use (i.e., in advance of administration to a subject in need thereof). Thus, in some embodiments, the present invention provides a liquid prasugrel composition comprising prasugrel and a cyclodextrin derivative, wherein the composition contains 10% or less of a prasugrel degradant after storage at about 25° C. for a period of at least 1 hour, at least 2 hours, at least 4 hours, at least 8 hours, at least 12 hours, at least 16 hours, or at least 24 hours.

Methods of Administering and Treating

In some embodiments, the present invention is directed to methods of delivering prasugrel to a subject in need thereof, the method comprising administering a pharmaceutical composition or unit dosage form of the present invention to the subject in need thereof. The methods of the present invention can include orally or parenterally administering the pharmaceutical compositions or unit dosage forms of the present invention.

In some embodiments, the present invention is directed to parenterally administering a pharmaceutical composition or unit dosage form of the present invention to a subject which an oral composition of prasugrel is, for one or more reasons, not appropriate. For example, oral compositions of prasugrel may not be appropriate because a subject may be too young, unable to swallow, undergoing surgery, incapacitated, or have a disorder that blocks absorption of prasugrel administered via the oral route. Further, parenteral administration of the pharmaceutical compositions of the present invention are useful for treating conditions in subject in which a rapid increase in the in vivo concentration of prasugrel is required, for example, within seconds or minutes of administering the drag. Moreover, parenteral administration can provide a more rapid onset than an orally administered formulation because prasugrel is delivered directly to the blood stream, avoiding gastrointestinal absorption and distribution.

In addition, titration to an effective dose of prasugrel in order to achieve a desired platelet aggregation inhibitory effect level is necessary in order to avoid excess adverse bleeding effects. Thus, a prasugrel formulation suitable for parenteral administration can effectively provide a more efficient dosage titration, thereby minimizing adverse bleeding events.

In some embodiments, the present invention is directed to a method of treating and or preventing diseases in a human subject by administering the pharmaceutical compositions and or unit dosage forms of the present invention to the human subject. In some embodiments, the present invention is directed to methods of treating a subject suffering from a disease or disorder amenable to treatment with prasugrel, the method comprising administering a pharmaceutical composition or unit dosage form to the subject. As used herein the terms "treat," "treating," and "treatment" refer to administering a composition of the present invention prior to the onset of clinical symptoms of a disease state/condition so as to prevent the development of any symptom, as well as administering the composition after the onset of one or more clinical symptoms of a disease state/condition so as to reduce or eliminate any such symptom, aspect or characteristic of the disease state/condition. Such treating need not be absolute to be useful. Additionally, the terms "treat" and "treatment" refer to both therapeutic treatment and prophylactic, maintenance, or preventative measures, wherein the object is to prevent or slow down (lessen) an undesired physiological condition, disorder or disease, or obtain beneficial or desired clinical results. For purposes of this invention, beneficial or desired clinical results include, but are not limited to, alleviation of a symptom or a sign; diminishment of extent of a condition, disorder or disease; stabilization (i.e., not worsening) of the state of condition, disorder or disease; delay in onset or slowing of condition, disorder or disease progression; amelioration of a condition, disorder or disease state, remission (whether partial or total), whether detectable or undetectable; or enhancement or improvement of condition, disorder or disease. Treatment includes eliciting a clinically significant response, without excessive levels of side effects. Treatment also includes prolonging survival as compared to expected survival if not receiving treatment.

As used herein, the term "subject" refers to warm blooded animals such as mammals, including humans and non-humans, such as, but not limited to, domestic and farm animals, zoo animals, sports animals, and pets (e.g., cats, dogs, mice, guinea pigs, horses, bovine cows, and sheep). In some embodiments, a subject is a human subject. Human subjects suitable for administering the pharmaceutical compositions and unit dosage forms of the present invention include, but are not limited to, pediatric, adult, geriatric and elderly subjects. In some embodiments of the invention, the subject is a pediatric subject. As used herein, a "pediatric" subject is up to 17 years of age, and includes neonates (0 to about 1 month of age), infants (about 1 month to about 2 years of age), children (about 2 to about 12 years of age) and adolescents (about 12 to 17 years of age). Adult subjects are at least 18 years of age. In some embodiments of the invention, the subject is an adult. In some embodiments of the invention, the subject is geriatric. Geriatric subjects are at least 65 years of age or older. Elderly subjects are at least 75 years of age or older.

In some embodiments, the present invention comprises a method for treating a subject who has or is at risk for developing a condition amenable to treatment with prasugrel, the method comprising administering an effective amount (i.e., a therapeutically effective amount) of a composition of the invention to the subject. A therapeutically effective amount of prasugrel can include administering about 0.001 mg/kg/day to about 1 mg/kg/day, about 0.01 mg/kg/day to about 0.5 mg/kg/day, about 0.05 mg/kg/day to about 0.5 mg/kg/day, about 0.05 mg/kg/day, or about 0.1 mg/kg/day.

In some embodiments, the present invention is directed to a method of treating a disease, disorder or condition having an etiology associated with platelet aggregation or of a disease, disorder or condition that is therapeutically responsive to prasugrel, the method comprising administering to a subject in need thereof a pharmaceutical composition or unit dosage form of the present invention.

In some embodiments, a method of the present invention comprises administering a pharmaceutical composition or unit dosage form to a subject that suffers from a disorder selected from: an acute coronary syndrome (e.g., unstable angina/non-Q-wave myocardial infarction, heart attack, angina, and the like), a recent myocardial infarction, a recent stroke, an established peripheral arterial disease, ST-segment elevation acute myocardial infarction, non-ST-segment elevation acute coronary syndrome, a recent percutaneous coronary intervention, a recent angioplasty, a thromboembolism, a pulmonary embolism, a deep vein thrombosis, atherosclerosis, diabetes mellitus, a transient ischemic event, a secondary ischemic event, vascular death with established peripheral arterial disease, cardiovascular disease, cerebrovascular disease, angina pectoris, cardiac arrhythmia, sickle cell crisis, and combinations thereof. Thus, the pharmaceutical compositions and unit dosage forms of the present invention are useful for treatment of a condition amenable to treatment with prasugrel, which include the above disorders and diseases. In some embodiments, the present invention comprises administering a pharmaceutical composition or unit dosage form to a subject that suffers from acute coronary syndrome, including subjects for whom percutaneous coronary intervention has been recommended or has occurred (with or without coronary stenting), or subjects for whom coronary artery bypass grafting has been recommended or has occurred.

The present invention is also directed to a method comprising administering a therapeutically effective amount of a pharmaceutical composition or unit dosage form to treat a subject in need thereof. For example, a therapeutically effective amount for the treatment of an acute coronary syndrome refers to an amount which, when administered, diminishes one or more symptoms associated with this disorder. In some embodiments, a method of the present invention comprises administering a unit dosage form of the present invention comprising a maintenance dose of about 1 mg to about 20 mg, about 1 mg to about 15 mg, or about 10 mg of prasugrel to a subject.

In some embodiments, the present invention is directed to a method of loading a subject to attain a therapeutically effective prasugrel concentration, the method comprising administering an effective amount of a pharmaceutical composition or unit dosage of the invention (e.g., intravenously or orally) to the subject. The present invention also includes treating a subject for whom oral prasugrel therapy has been interrupted (intentionally or unintentionally). Thus, the pharmaceutical compositions and unit dosage forms of the present invention are useful for treating a subject who needs to rapidly attain or re-attain a pre-determined (i.e., targeted or desired) plasma prasugrel concentration, e.g., when a concentration of prasugrel has declined as a result of not taking a prasugrel maintenance dose for a period of time. For example, a composition of the present invention can be parenterally administered to a subject upon re-starting administration of prasugrel as either of an adjunctive or a monotherapy in a subject. Therefore, in some embodiments the present invention is directed to administering a unit dosage form of the present invention comprising a loading dose of about 20 mg to about 120 mg, about 20 mg to about 100 mg, about 40 mg to about 80 mg, or about 60 mg of prasugrel to a subject. In some embodiments, the present invention is directed to providing a loading dose of prasugrel, in which a dose of prasugrel is parenterally administered to a subject to provide a predetermined blood systemic concentration of prasugrel.

In some embodiments, the present invention is directed to a method for titrating a subject in need thereof to a therapeutically effective dose of prasugrel, the method comprising: parenterally administering a first dose of the pharmaceutical composition of the present invention to the subject in need thereof; determining the subject's responsiveness to the first dose of the pharmaceutical composition; and parenterally administering a second dose of the pharmaceutical composition to the subject, wherein the second dose comprises an increased or decreased amount of prasugrel compared to the first dose. In some embodiments, the method comprises: repeating the determining, and parenterally administering further doses of the pharmaceutical composition of the present invention until a desired therapeutic effectiveness is achieved. A desired therapeutic effectiveness can comprise achieving a desired or predetermined level of platelet aggregation in a subject's plasma.

In some embodiments, the method for titrating is administered to a subject in need thereof with a history of stroke or transient ischemic attack, an elderly subject, or a subject having a body mass less than about 60 kg.

Determining a subject's responsiveness to prasugrel can comprise: obtaining a blood sample from the subject; and determining the extent of platelet aggregation in the subject's plasma. Suitable methods for determining the extent of platelet aggregation in the subject's plasma include, for example, aggregometry, such as light transmittance or impedance aggregometry, and other methods known to persons of ordinary skill in the art.

Not being bound by any particular theory, titrating a subject in need thereof to a therapeutically effective prasugrel dose can be more safely and efficiently achieved using the pharmaceutical compositions of the present invention due to, inter alia, faster therapeutic onset provided by a parenterally administered prasugrel dose, enhanced bioavailability provided by a pharmaceutical composition of the present invention, a faster rate of onset provided by a pharmaceutical composition of the present invention compared to a composition lacking a cyclodextrin derivative, and combinations thereof. Thus, a parenterally administered prasugrel composition can enable a lower first dose of prasugrel to be administered to a subject in need thereof, followed by determination of the therapeutic effect of the first dose of prasugrel, for example, by determining the platelet aggregation inhibition effect of the first prasugrel dose. The prasugrel dose necessary to achieve a desired therapeutic effect can therefore be achieved more safely and efficiently, and as a result can substantially decrease the rate of adverse bleeding events in at-risk patient populations.

In some embodiments, an initial dose prasugrel suitable for titrating to a therapeutically effective dose of prasugrel is about 1 mg to about 0.60 mg, about 2 mg to about 60 mg, about 5 mg to about 60 mg, about 10 mg to about 60 mg, about 15 mg to about 60 mg, about 20 mg to about 60 mg, about 30 mg to about 60 mg, about 50 mg to about 60 mg, about 1 mg to about 50 mg, about 2 mg to about 40 mg, about 5 mg to about 30 mg, about 10 mg to about 20 mg, about 1 mg, about 2 mg, about 2.5 mg, about 5 mg, about 7.5 mg, about 10 mg, about 15 mg, about 20 mg, about 30 mg, about 40 mg, about 50 mg, or about 60 mg prasugrel.

The pharmaceutical compositions and unit dosage forms of the present invention can be administered alone or in conjunction with other medications or pharmaceutical compositions. In some embodiments, a method of the present invention comprises administering to a subject a nonsteroidal antiinflammatory drug, a selective factor Xa inhibitor, a direct thrombin inhibitor, a prostaglandin analog, an adenosine diphosphate (ADP) inhibitor, a platelet aggregation inhibitor, an antiplatelet agent, a glycoprotein IIb/IIIa inhibitor or antagonist, an antisickling agent, a hemorrheologic agent, a thrombolytic agent, a thrombolytic enzyme, a thromboxane A2 biosynthesis inhibitors, a thromboxane antagonist, a cyclooxygenase inhibitor, an angiotensin antagonist, an endothelin antagonist, a phosphodiesterase inhibitor, an angiotensin converting enzyme (ACE) inhibitors, a neutral endopeptidase inhibitors, an anticoagulants, a diuretic, a tissue plasminogen activator, a modified tissue plasminogen activator, a biologic response modifier, a statin, a calcium channel blocking agent, an anti-arrhythmic agent, an α-adrenergic agonist, a β-adrenergic antagonist, and combinations thereof.

In some embodiments, a method of the present invention comprises administering to a subject a second therapeutic agent selected from: an analog or derivative of prasugrel, clopidogrel, diclofenac, droxicam, etolodac, fenoprofen, flurbiprofen, indomethacin, isoxicam, ketoprofen, lornoxicam, meloxicam, mefenamate, naproxen, oxaprozin, piroxicam, sulindac, tenoxicam, apixaban, otamixaban, rivaroxaban, eptifibatide, beraprost, prostacyclin, iloprost, treprostinil, ticagrelor, ticlopidine, abciximab, cloricromen, ditazole, indobufen, picotamide, sulfinpyrazone, abciximab, eptifibatide, tirofiban, cetiedil, alteplase, anistreplase, brinase, drotrecogin alfa, monteplase, reteplase, saruplase, streptokinase, tenecteplase, urokinase, fibrinolysin, ancrod, aspirin, picotamide, ramatroban, seratrodast, aloxiprin, carbasalate calcium, celecoxib, ibuprofen, rofecoxib, candesartan, eprosartan, irbesartran, losartan, olmesartan, telmisartan, valsartan, ambrisentan, atrasentan, bosentan, sitaxentan, tezosentan, cilostazol, dipyridamole, enoximone, milrinone, captopril, enalapril, enaliprilat, spirapril, quinapril, perindopril, ramipril, fosinopril, trandolapril, lisinopril, moexipril, benazepril, candoxatril, ecadotril, candoxatril, ecadotril, unfractionated heparin, ardeparin, bemiparin, certoparin, dalteparin, enoxaparin, fondaparin, fragmin, melagatran, nadroparin, parnaparin, reviparin, tinzaparin, argatroban, dabigatran, melagatran, ximelagatran, defibrotide, ramatroban, antithrombin III, fondaparinux, idraparinux, danaparoid, sulodexide, dermatan sulfate, a synthetic pentasaccharide, a hirudin, disulfatohirudin bivalirudin, desirudin, lepirudin, acenocoumarol, coumatetralyl, dicoumarol, ethyl biscoumacetate, phenprocoumon, clorindione, diphenadione, phenindione, tioclomarol, warfarin, chlorothiazide, hydrochlorothiazide, ethacrynic acid, furosemide, amiloride, chlorothiazide, hydrochlorothiazide, atorvastatin, fluvastatin, lovastatin, pravastatin, pravastatin, rosuvastatin, simvastatin, amlodipine, felodipine, diltiazem, nifedipine, nicardipine, nisoldipine, bepridil, verapamil, dofetilide, ibutilide, metoprolol, propranolol, atenolol, betaxolol, bisoprolol, carvediol, nadolol, nebivolol, timolol, ajmaline, disopyramide, prajmaline, procainamide, quinidine, sparteine, aprindine, lidocaine, mexiletine, tocainide, encainide, flecainide, lorcainide, moricizine, propafenone, acebutolol, pindolol, amiodarone, bretylium, bunaftine, dofetilide, sotalol, adenosine, atropine, digoxin, doxazosin, terazosin, prazosin, and combinations thereof.

In some embodiments, the pharmaceutical compositions and unit dosage forms of the present invention can enhance the bioavailability, rate of therapeutic onset, and/or therapeutic efficacy of prasugrel. Thus, the present invention is also directed to a method of decreasing the time to therapeutic onset of prasugrel following administration thereof, the method comprising orally or parenterally administering to a subject in need thereof a pharmaceutical composition or unit dosage form of the present invention, wherein the time to therapeutic onset of prasugrel provided by the orally or parenterally administered composition or unit dosage is less than the time to therapeutic onset of prasugrel provided by an orally administered reference composition that excludes the cyclodextrin derivative and contains an equivalent dose of prasugrel. In some embodiments, the time to therapeutic onset of prasugrel following administration of a pharmaceutical composition or unit dosage form of the present invention is reduced by at least 5%, at least 10%, at least 15%, at least 20%, at least 25%, at least 30%, at least 40%, or at least 50% compared to the time to therapeutic onset of prasugrel provided by an orally administered reference composition that excludes the cyclodextrin derivative and contains an equivalent dose of prasugrel.

In some embodiments, the dissolution of prasugrel from the dosage forms of the present invention can be related to pharmacokinetic parameters and/or the in vivo concentration of prasugrel and/or its metabolite(s). The in vivo concentration of prasugrel and its metabolite(s), as well as pharmacokinetic parameters associated with an active form of prasugrel can be determined by, e.g., sampling the blood plasma of a subject after administering a composition of the present invention. Pharmacokinetic parameters that can be measured include, but are not limited to, $AUC_t$, $AUC_{inf}$, and $\ln(AUC_{LAST})$.

As used herein, "$AUC_t$" refers to the Area Under the Concentration time curve (i.e., plot of plasma concentration vs. time) after prasugrel administration. The area is conveniently determined by the "trapezoidal rule": the data points are connected by straight line segments, perpendiculars are erected from the abscissa to each data point, and the sum of the areas of the triangles and trapezoids so constructed is computed.

As used herein, "$AUC_{inf}$" refers to the Area Under the Concentration time curve, wherein the last concentration is extrapolated to baseline based on the rate constant for elimination.

As used herein, "$\ln(AUC_{LAST})$" refers to the Area Under the Concentration time curve determined by plotting plasma concentration on a natural logarithmic scale, using the last measured plasma concentration as the end point.

As used herein, "IntraCV" refers to an intra-assay coefficient of variation, which is the standard deviation within a sample set divided by the mean value of the sample set, with the result reported as a percentage.

In some embodiments, the bioavailability of prasugrel from a composition of the present invention is substantially equivalent to that observed upon administration of EFFIENT® (Eli Lilly & Co., Indianapolis, Ind.) pharmaceutical preparations that contain an equivalent dosage of prasugrel. For example, the dosage forms of the present invention can have an $AUC_t$ or $AUC_{inf}$ which is within about 80% to about 120%, about 90% to about 110%, about 95% to about 105%, or approximately equivalent to that observed when EFFIENT® pharmaceutical preparations are administered at an equivalent dosage.

In some embodiments, the bioavailability of prasugrel from a composition of the present invention is greater than that observed upon administration of EFFIENT® pharmaceutical preparations that contain an equivalent dosage of prasugrel. For example, the dosage forms of the present invention can have an $AUC_t$ or $AUC_{inf}$ that is about 5%, about 10%, about 15%, about 20%, about 25%, or about 30% greater than that observed when EFFIENT® pharmaceutical preparations are administered at an equivalent dosage.

In some embodiments, the rate of therapeutic onset of prasugrel from a composition of the present invention is faster than that observed upon administration of EFFIENT® pharmaceutical preparations that contain an equivalent dosage of prasugrel. For example, the dosage forms of the present invention can have a time to $C_{max}$ that is about 5%, about 10%, about 15%, about 20%, about 25%, or about 30% faster than that the time for $C_{max}$ that is observed upon administration of an EFFIENT® pharmaceutical preparation at an equivalent dosage.

Having generally described the invention, a further understanding can be obtained by reference to the examples provided herein. These examples are given for purposes of illustration only and are not intended to be limiting.

EXAMPLES

Example 1

The solubility of prasugrel between pH 1 and 14 was determined using the General Solubility Equation (see, e.g., T. Sanghvi et al., *QSAR & Combinatorial Science* 22:258 (2003)). The calculations were performed using ACD® software (Advance Chemistry Development Inc., Toronto, Canada) using the following data: Log P=3.17, pKa=4.07, and melting point=112-114° C. The results are depicted graphically in FIG. 1. Referring to FIG. 1, a plot of prasugrel solubility (Log solubility, mg/mL) versus pH is provided. The intrinsic solubility of prasugrel calculated using the general solubility equation is about 0.1 mg/mL at about pH 5 and above. As shown, the solubility of prasugrel increases at or below about pH 4.

Example 2

The weight:volume phase solubility of prasugrel in an aqueous solution that contained varying amounts of a sulfoalkyl ether cyclodextrin (β-cyclodextrin derivatized with sulfobutyl ether groups having an ADS of about 6.5, $SBE_{6.5}$-β-CD) at pH 7.4 was determined.

The results of the phase solubility study at pH 7.4 are listed in the following table:

| $SBE_{6.5}$-β-CD conc. (% w/v) | Prasugrel Solubility (mg/mL) | Prasugrel Solubility (% w/v) | CD:Prasugrel Ratio (w/w) |
| --- | --- | --- | --- |
| 0 | 0 | 0 | n/a |
| 5% | 0.054 | 0.0054% | 926:1 |
| 10% | 0.124 | 0.0124% | 806:1 |
| 20% | 0.252 | 0.0252% | 793:1 |
| 30% | 0.379 | 0.0379% | 791:1 |
| 40% | 0.515 | 0.515% | 777:1 |

Figure 2:
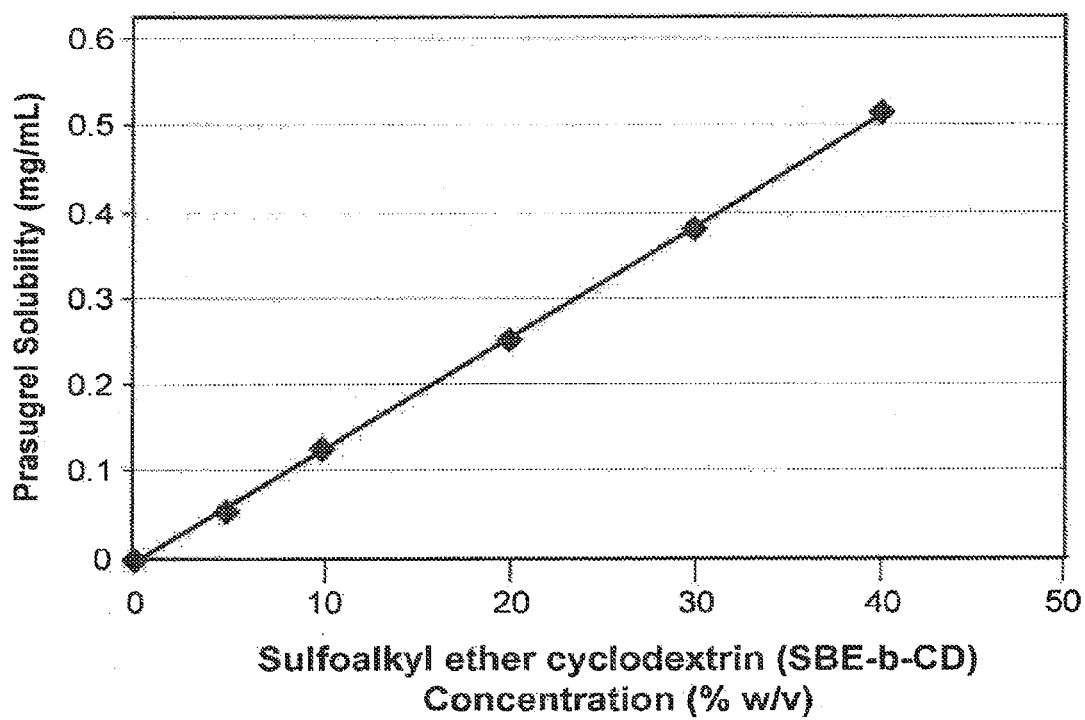
FIG. 2 provides a graphic representation of the phase solubility (mg/mL) of prasugrel in aqueous solution at pH 7.4, as a function of sulfoalkyl ether cyclodextrin concentration (% w/v) for $SBE_{6.5}$-β-CD.

The results of the phase solubility study at pH 7.4 are also depicted graphically in FIG. 2. Referring to FIG. 2, the prasugrel solubility increased linearly as a function of the derivatized cyclodextrin concentration.

Example 3

The phase solubility of prasugrel in an aqueous solution that contained varying amounts of a sulfoalkyl ether cyclodextrin (β-cyclodextrin derivatized with sulfobutyl ether groups having an ADS of about 6.5, $SBE_{6.5}$-β-CD) or a hydroxypropyl ether cyclodextrin (β-cyclodextrin derivatized with 2-hydroxypropyl ether groups having an ADS of about 4.3, $HP_{4.3}$-β-CD) at pH 4 was determined.

The results of the phase solubility study at pH 4 are listed in the following table:

| Cyclodextrin Derivative Conc. (% w/v) | Prasugrel Solubility w/$HP_{4.3}$-β-CD (mg/mL) | Prasugrel Solubility w/$SBE_{6.5}$-β-CD (mg/mL) | $SBE_{6.5}$-β-CD to Prasugrel Ratio (w/w) |
| --- | --- | --- | --- |
| 0 | 0.206 | 0.206 | n/a |
| 5% | 0.256 | 0.268 | 187:1 |
| 10% | 0.474 | 0.736 | 136:1 |
| 20% | 0.524 | 0.58 | 345:1 |
| 30% | 0.645 | 0.664 | 452:1 |
| 40% | 0.875 | 0.927 | 431:1 |

Figure 3:
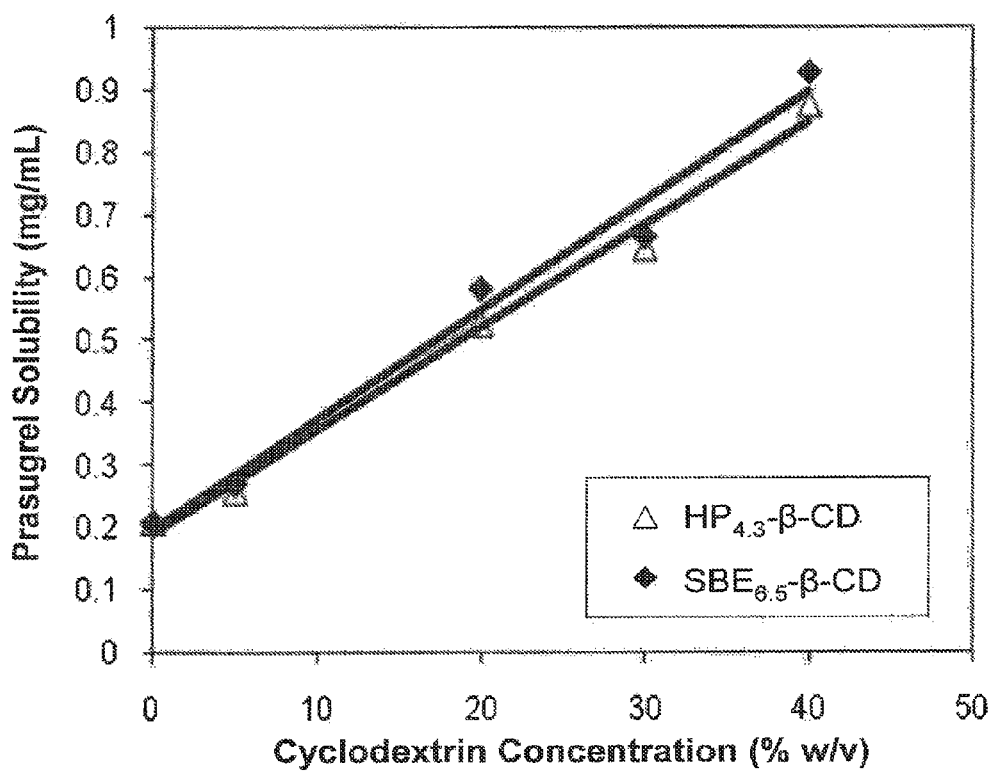
FIG. 3 provides a graphic representation of phase solubility (mg/mL) of prasugrel in aqueous solution at pH 4, as a function of cyclodextrin derivative concentration (% w/v) for $HP_{4.3}$-β-CD and $SBE_{6.5}$-β-CD.

The results of the phase solubility study at pH 4 are also depicted graphically in FIG. 3. Referring to FIG. 3, the prasugrel solubility increased linearly as a function of the derivatized cyclodextrin concentration for both hydroxypropyl ether- and sulfobutyl ether-derivatized β-cyclodextrins. Note that the data obtained for the 10% w/v cyclodextrin derivatives was not included in the best-fit line that appears in FIG. 3.

Figure 4:
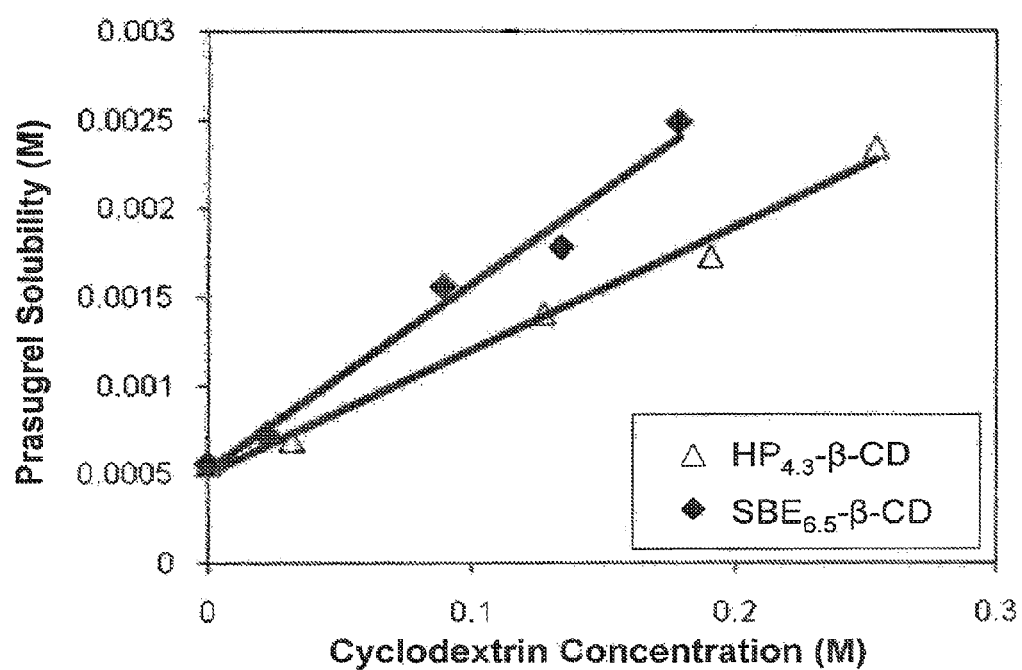
FIG. 4 provides a graphic representation of phase solubility (M) of prasugrel in aqueous solution at pH 4, as a function of cyclodextrin derivative concentration (M) for $HP_{4.3}$-β-CD and $SBE_{6.5}$-β-CD.

The molar prasugrel phase solubility in aqueous solution at pH 4 that contains varying concentrations of hydroxypropyl ether- and sulfobutyl ether-derivatized β-cyclodextrins is displayed in FIG. 4. Referring to FIG. 4, the molar solubility of prasugrel increases linearly with respect the molar concentration of both hydroxypropyl ether β-cyclodextrin and sulfobutyl ether β-cyclodextrin. Comparison of the data the slopes of the best-fit lines for the prasugrel solubility as a function of the derivatized cyclodextrin concentration shows that the $SBE_{6.5}$-β-CD provides improved solubilization of prasugrel on a molar basis, compared to $HP_{4.3}$-β-CD.

Example 4

The phase solubility of prasugrel in an aqueous solution that contained 20% w/v of various derivatized cyclodextrins at pH 4 was determined. The cyclodextrin derivatives examined were as follows: α-cyclodextrin derivatized with sulfopropyl ether groups having an ADS of about 5.1 ($SPE_{5.1}$-α-CD), β-cyclodextrin derivatized with sulfopropyl ether groups having an ADS of about 5.6 ($SPE_{5.6}$-β-CD), γ-cyclodextrin derivatized with sulfopropyl ether groups having an ADS of about 5.4 ($SPE_{5.4}$-γ-CD), β-cyclodextrin derivatized with sulfobutyl ether groups having an ADS of about 4.9 ($SBE_{4.9}$-β-CD), β-cyclodextrin derivatized with sulfobutyl ether groups having an ADS of about 7 ($SBE_7$-β-CD), γ-cyclodextrin derivatized with sulfobutyl ether groups having an ADS of about 6.1 ($SBE_{6.1}$-γ-CD), and β-cyclodextrin derivatized with hydroxypropyl ether groups having an ADS of about 7.5 ($HP_{7.5}$-β-CD).

The phase solubility data is listed in the following table:

| Cyclodextrin Derivative | Prasugrel Solubility (mg/mL) | Prasugrel Solubility (% w/v) | CD to Prasugrel Ratio w/w |
|---|---|---|---|
| $SPE_{5.1}$-α-CD | 1.92 | 0.192% | 104:1 |
| $SPE_{5.6}$-β-CD | 0.96 | 0.096% | 209:1 |
| $SPE_{5.4}$-γ-CD | 0.90 | 0.09% | 221:1 |
| $SBE_{4.9}$-β-CD | 0.69 | 0.069% | 288:1 |
| $SBE_7$-β-CD | 0.59 | 0.059% | 336:1 |
| $SBE_{6.1}$-γ-CD | 0.29 | 0.029% | 680:1 |
| $HP_{7.5}$-β-CD | 0.54 | 0.054% | 373:1 |

Example 5

Figure 5:
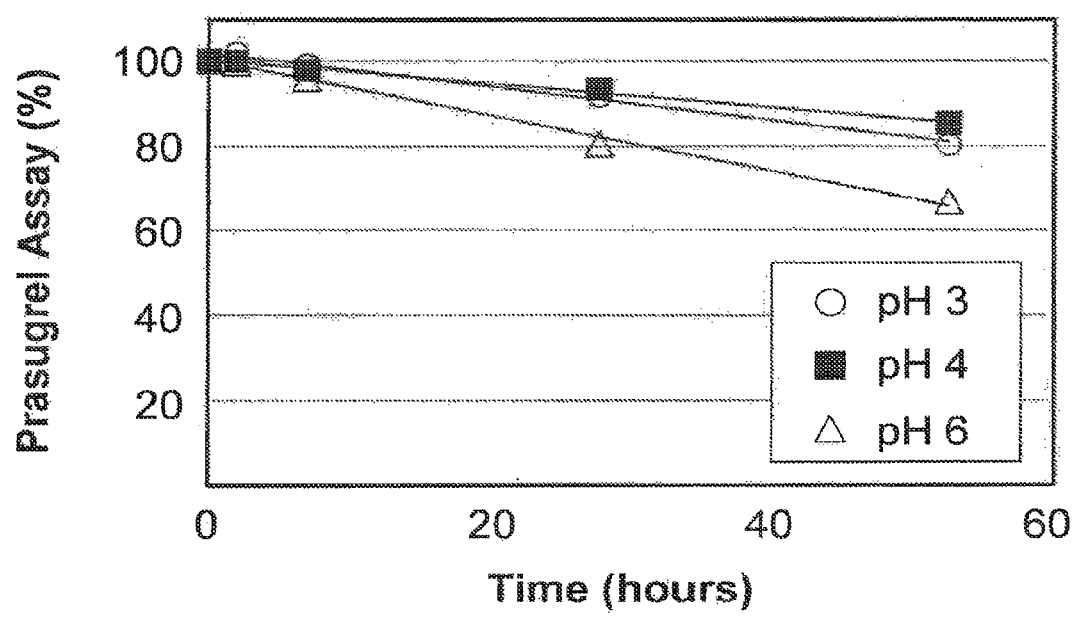
FIGS. 5 and 6 provide graphic representations of the stability of prasugrel in aqueous solutions at various pH, the aqueous solutions containing cyclodextrin derivatives.

The stability of prasugrel in an aqueous solution that contained 30% w/v of $SBE_{6.5}$-β-CD, buffered at pH 3, pH 4 and pH 6 using 0.1 M phosphate buffer was determined. The initial prasugrel concentration was 0.09 mg/mL (pH 3), 0.062 mg/mL (pH 4), and 0.048 mg/mL (pH 6). The solutions were sampled at 0, 2, 7 and 53 hours. The prasugrel assay was determined using a Shimadzu LC20AD HPLC with UV/vis detector (detection wavelength, λ=220 nm). The data obtained from the stability study is provided graphically in FIG. 5. Referring to FIG. 5, the prasugrel in the 30% w/v $SBE_{6.5}$-β-CD solution at pH 3 and 4 exhibited a decrease in prasugrel concentration of less than 10% after 30 hours and less than 20% after about 55 hours. The prasugrel in the 30% w/v $SBE_{6.5}$-β-CD solution at pH 6 exhibited a decrease in prasugrel concentration of about 20% after 30 hours, and about 36% after about 55 hours. The data indicates that prasugrel in an aqueous solution containing a sulfoalkyl ether-β-cyclodextrin is more stable at pH 4 or less.

Example 6

Figure 6:
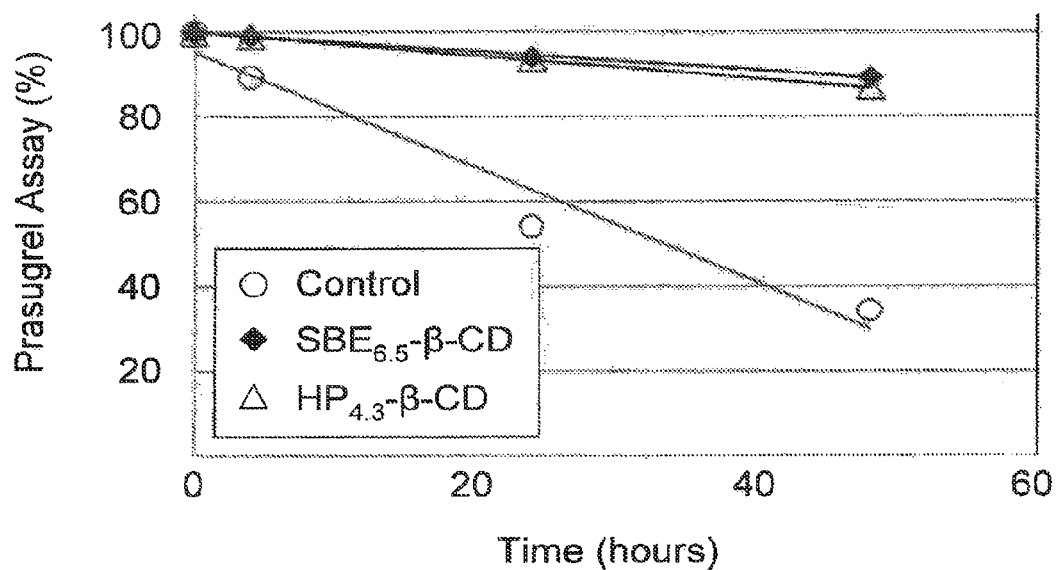

The stability of prasugrel in an aqueous solution that contained 30% w/v of $SBE_{6.5}$-β-CD or $HP_{4.3}$-β-CD, buffered at pH 4 using 0.1 M phosphate buffer was determined. The initial prasugrel concentration was 0.06 mg/mL. The solutions were sampled at 0, 4, 24 and 48 hours. The prasugrel assay was determined using the protocol described in Example 4. The data obtained from the stability study is provided graphically in FIG. 6. Referring to FIG. 6, the prasugrel in the 30% w/v solutions of $SBE_{6.5}$-β-CD and $HP_{4.3}$-β-CD at pH 4 exhibited a nearly identical stability. The prasugrel in the 30% w/v $SBE_{6.5}$-β-CD solution at pH 6 exhibited a decrease in prasugrel concentration of about 20% after 90 hours, and about 36% after 163 hours. The data indicates that prasugrel in an aqueous solution containing a sulfoalkyl ether-β-cyclodextrin is more stable at pH 4 or less.

Prophetic Example A

An aqueous prasugrel formulation suitable for parenteral administration to a subject in need thereof will be prepared as follows: SBE-β-CD (DS=6.5±0.5) (87.5 g±12.5 g) will be added to approximately 200 mL of a phosphate buffer solution (0.1 M), and will be mixed at room temperature until completely dissolved. Prasugrel (250 mg) will be added to the solution, which will be stirred at room temperature until the solution is clear. The clear solution will be diluted to a final volume of 250 mL by adding an additional 50 mL of phosphate buffer (0.1 M). The pH of the resulting aqueous solution will be adjusted to pH 4±0.5 by adding an appropriate amount of HCl or NaOH.

The components of the aqueous prasugrel formulation are provided in detail in the following table:

| Ingredient | Amount [Concentration] |
|---|---|
| Prasugrel | 250 mg [0.1% w/v] |
| SBE7-β-CD | 87.5 g [35% w/v] |
| Phosphate buffer | [0.1M] |
| HCl/NaOH | to provide pH 4 ± 0.5 |

Prophetic Example B

The aqueous solution of prasugrel prepared in Prophetic Example A will be used to prepare a lyophilized prasugrel formulation suitable for storage at room temperature, and capable of being diluted with, e.g., sodium chloride for injection, USP, for parenteral administration to a subject in need thereof. The aqueous formulation containing prasugrel in a concentration of 0.1% w/v and SBE-β-CD [DS=6.51±0.5] in a concentration of 35%±5.0% w/v will be transferred in 60 mL aliquots to 100 mL serum vials. The filled serum vials will be transferred to a freeze dryer, e.g., a FTS Systems' DURA-DRY™ tray dryer attached to a DURA-DRY™ II MP Condenser Module, and lyophilized to provide a free-flowing powder. The lyophilized formulation can be reconstituted using about 10 mL to about 100 mL of sterile water, or another pharmaceutically acceptable diluent, to provide a clear solution suitable for parenteral administration.

Prophetic Example C

An aqueous prasugrel formulation suitable for parenteral administration to a subject in need thereof will be prepared as follows: SBE-β-CD (DS=6.5±0.5) (45 g±10 g) will be added to approximately 200 mL of a phosphate buffer solution (0.1 M), and will be mixed at room temperature until completely dissolved. Prasugrel (125 mg) will be added to the solution, which will be stirred at room temperature until the solution is clear. The clear solution will be diluted to a final volume of 250 mL by adding an additional 50 mL of phosphate buffer (0.1 M). The pH of the resulting aqueous solution will be adjusted to pH 4±0.5 by adding an appropriate amount of HCl or NaOH.

The components of the aqueous prasugrel formulation are provided in detail in the following table:

| Ingredient | Amount [Concentration] |
| --- | --- |
| Prasugrel | 125 mg [0.05% w/v] |
| SBE7-β-CD | 45 g [18% w/v] |
| Phosphate buffer | [0.1M] |
| HCl/NaOH | to provide pH 4 ± 0.5 |

Prophetic Example D

A pharmaceutical composition of the present invention will be administered to dogs in order to determine pharmacokinetic parameters, and efficacy of inhibition of platelet aggregation.
Study Ethics
All experiments will be conducted in accordance with the *Guide for the Care and Use of Laboratory Animals* published by the U.S. National Institutes of Health (NIH Pub. No. 85-23, revised 1996).
Animals
Female beagle dogs (n=3 for each cohort) between 7 and 11 months of age (weighing about 8 kg) will be used in this study. The animals will be obtained from Covance Research Products (Kalamazoo, Mich.) or another suitable source. The dogs will be housed in pens and kept on an alternating 12/12 hours light/dark cycle. Each animal will receive 215 g/day of a 25% protein diet and each animal will have free access to water.
Study Drugs
The prasugrel formulation will be a lyophilized solid that contains prasugrel (60 mg/vial) and a sulfobutylether-β-cyclodextrin having an average degree of substitution of about 6.5 (CAPITSOL®, 21 g/vial), provided by CyDex Pharmaceuticals, Inc. (Lenexa, Kans.). The lyophilized solid will be prepared from a solution comprising a 100 mM phosphate buffer having a pH of about 4. The lyophilized solid will be reconstituted immediately prior to administration by contacting the solid with 10 mL to 100 mL of sterile water, or another pharmaceutically acceptable diluent, to provide a prasugrel formulation that contains 0.6 mg/mL to 6 mg/mL of prasugrel and 0.21 g/mL to 2.1 g/mL of the sulfobutylether-β-cyclodextrin. The prasugrel formulation will be administered to 3 dogs at a dose of about 1 mg/kg (i.e., 1 mg of prasugrel per 1 kg body weight) as a bolus push through a previously implanted venous cannula.

A control group of animals will be administered a prasugrel formulation lacking the cyclodextrin derivative (EFFIENT®, Eli Lilly & Co., Indianapolis, Ind.). The cyclodextrin-free prasugrel formulation will be administered to 3 dogs at a dose of about 1 mg/kg as an oral gavage through a stomach tube. The stomach tube will be rinsed with tap water (10 mL) after each administration.
Study Design
After an overnight fast, morphine (1 mg/kg, s.c.) will be administered and the dogs will be placed under general anesthesia using α-chloralose (120 mg/kg, i.v.). The anesthesia will be maintained by a constant infusion of α-chloralose (35 mg/kg/h to 75 mg/kg/h, i.v.) through an indwelling catheter in the saphenous or cephalic vein. At the conclusion of each experiment, the dogs will be euthanized by barbiturate overdose while under general anesthesia.

Blood samples (approximately 1 mL) from a venous cannula will be collected pre-dose (baseline) and then at 10, 20, 30, and 60 minutes, and at 2, 3, and 5 hours after the prasugrel dose. The blood samples will be collected into K3 EDTA sample tubes for pharmacokinetic analysis. The tubes will be spun in a refrigerated centrifuge and the plasma will be stored at −70° C. until the analysis is conducted. Plasma concentrations of prasugrel and its thiol metabolites (Smith et al., *Xenobiotica* 37:884-901 (2007)) will be determined using liquid chromatography with tandem mass spectrometric detection (LC/MS/MS, Finnigan LCQ DECA, positive ion electrospray mode). Samples will be prepared for injection by protein precipitation with acetonitrile. The method outlined above or another suitable method will be used.

Blood samples (approximately 10 mL) from a venous cannula will also be collected into sodium citrate sample tubes pre-dose (baseline) and then at 10, 20, 30, 60 minutes, and at 2, 3, and 5 hours after the prasugrel dose. Platelet aggregation determinations are performed on these samples as described by Heiman et al., *Br. J. Pharmacol.* 136:927-937 (2002)

Specifically, blood (10 mL) will be withdrawn from the right femoral vein cannula into a plastic syringe containing trisodium citrate solution (3.7%) as an anticoagulant (1:10 citrate to blood, v/v; final concentration, 0.37% by volume) for the ex vivo platelet aggregation determinations. Heparinized blood (10 mL; 10 U/mL of blood) also is collected for platelet aggregation studies. The whole-blood cell count will be determined with an H-10 cell counter (Texas International Laboratories, Inc.). Platelet rich plasma, the supernatant present after centrifugation of anticoagulated whole blood at 1000 rpm for 5 minutes (140 g), will be diluted with platelet-poor plasma to achieve a platelet count of 200,000/mm$^3$. Platelet-poor plasma will be prepared after the platelet-rich plasma is removed by centrifuging the remaining blood at 2000 g for 10 minutes and discarding the bottom cellular layer. Ex vivo platelet aggregation will be assessed by established spectrophotometric methods with a 4-channel aggregometer (BioData-PAP-4, Bio Data Corp.) by recording the increase in light transmission through a stirred suspension of platelet-rich plasma maintained at about 37° C. Aggregation will be induced with ADP (20 μM). A subaggregatory concentration of epinephrine (550 nM) will be used to prime the platelets before addition of the agonists. Values for platelet aggregation will be expressed as a percentage of light transmission standardized to the platelet-rich plasma sample (T=0% light transmission) and platelet-poor plasma sample (T=100% light transmission).

CONCLUSION

These examples illustrate possible embodiments of the present invention. While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A pharmaceutical composition comprising:
prasugrel, and
a cyclodextrin derivative of Formula I:

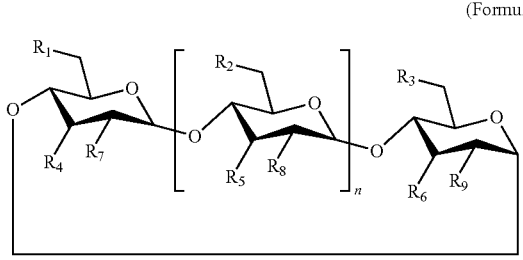

(Formula I)

wherein
the cyclodextrin derivative is present in a ratio of 100:1 to 700:1 by weight relative to the prasugrel;
n is 4, 5 or 6;
$R_1$, $R_2$, $R_3$, $R_4$, $R_5$, $R_6$, $R_7$, $R_8$ and $R_9$ are independently selected from: —OH, a straight-chain or branched —O—($C_1$-$C_8$-(alkylene))-$SO_3^-$ group, a substituted or unsubstituted straight-chain, branched, or cyclic —O—($C_1$-$C_{10}$) group, a substituted straight-chain, branched, or cyclic —S—($C_1$-$C_{10}$) group, and a saccharide; and
wherein the composition is formulated for oral or parenteral administration.

2. The pharmaceutical composition of claim 1, further comprising at least one pharmaceutically acceptable excipient.

3. The pharmaceutical composition of claim 1, wherein the bioavailability of the prasugrel in the composition is greater than an equimolar amount of prasugrel alone.

4. The pharmaceutical composition of claim 2, wherein the time to therapeutic onset of prasugrel is reduced by at least 20%.

5. The pharmaceutical composition of claim 1, wherein the cyclodextrin derivative is present in a concentration of at least 50:1 by mole relative to the prasugrel.

6. The pharmaceutical composition of claim 1, wherein the pharmaceutical composition has a pH of 2 to 4.

7. The pharmaceutical composition of claim 1, wherein the pharmaceutical composition has a pH of 4 to 9.

8. A pharmaceutical composition comprising
prasugrel, and
a cyclodextrin derivative of Formula I:

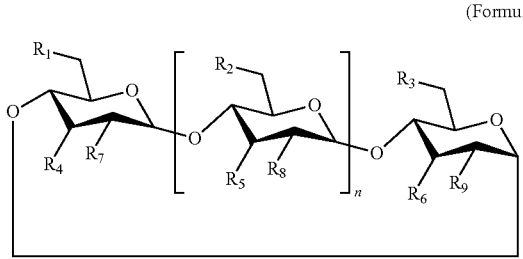

(Formula I)

wherein the cyclodextrin derivative is present in a ratio of at least 700:1 by weight relative to the prasugrel;
n is 4, 5 or 6;
$R_1$, $R_2$, $R_3$, $R_4$, $R_5$, $R_6$, $R_7$, $R_8$ and $R_9$ are independently selected from: —OH, a straight-chain or branched —O—($C_1$-$C_8$-(alkylene))-$SO_3^-$ group, a substituted or unsubstituted straight-chain, branched, or cyclic —O—($C_1$-$C_{10}$) group, a substituted straight-chain, branched, or cyclic —S—($C_1$-$C_{10}$) group, and a saccharide; and
wherein the composition is formulated for oral or parenteral administration.

9. The pharmaceutical composition of any of claim 1, wherein at least one of $R_1$, $R_2$, $R_3$, $R_4$, $R_5$, $R_4$, $R_7$, $R_8$ and $R_9$ is a —O-(hydroxy-substituted-$C_3$) group.

10. The pharmaceutical composition of any of claim 1, wherein $R_1$, $R_2$, $R_3$, $R_4$, $R_5$, $R_6$, $R_7$, $R_8$ and $R_9$ are independently —OH or a straight-chain or branched —O—($C_1$-$C_8$-(alkylene))-$SO_3^-$ group, and wherein the degree of substitution with a straight-chain or branched —O—($C_1$-$C_8$-(alkylene))-$SO_3^-$ group is 4 to 8 per cyclodextrin derivative.

11. The pharmaceutical composition of claim 1, wherein at least one of $R_1$, $R_2$, $R_3$, $R_4$, $R_5$, $R_6$, $R_7$, $R_8$ and $R_9$ is substituted with a —O-(straight-chain C4-(alkylene))-$SO_3^-$ group.

12. The pharmaceutical composition of claim 1, wherein the cyclodextrin derivative is a compound of formula II:

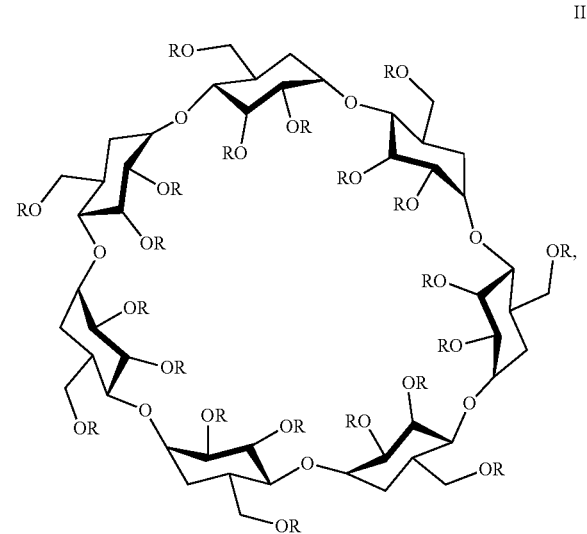

II wherein R=$(H)_{21-x}$ or $(—(CH_2)_4—SO_3^-Na^+)_x$, and wherein x=6.0-7.1.

13. The pharmaceutical composition of claim 1, comprising an agent selected from: a carrier, a diluent, a preservative, an antioxidant, a second therapeutic agent, an acidifying agent, an alkalinizing agent, a buffering agent, a bulking agent, a complexation enhancing agent, a cryoprotectant, a density modifier, an electrolyte, a flavor, a fragrance, a lyophilizing aid, a plasticizer, a solubility-enhancing agent, a stabilizing agent, a surface tension modifier, a volatility modifier, a viscosity modifier, and combinations thereof.

14. The pharmaceutical composition of claim 1, further comprising a sweetener.

15. The pharmaceutical composition of claim 1, wherein the composition is selected from the group consisting of a solution, a suspension, and an emulsion.

16. The pharmaceutical composition of claim 1, wherein the composition further comprises 1 mg to 120 mg of prasugrel.

17. A method of treating a disease, disorder or condition having an etiology associated with platelet aggregation or of a disease, disorder or condition that is therapeutically responsive to prasugrel, comprising administering a pharmaceutical composition according to claim 2 to a subject in need thereof.

18. The method of claim 17, wherein the composition is administered as a unit dosage form comprising a maintenance dose of 1 mg to 20 mg of prasugrel.

19. The method of claim 17, wherein the composition is administered as a unit dosage form comprising a loading dose comprising 20 mg to 120 mg of prasugrel.

20. The method of claim 17, wherein the disorder is selected from: an acute coronary syndrome, a recent myocardial infarction, a recent stroke, an established peripheral arterial disease, ST-segment elevation acute myocardial infarction, non-ST-segment elevation acute coronary syndrome, a recent percutaneous coronary intervention, a recent angioplasty, a thromboembolism, a pulmonary embolism, a deep vein thrombosis, atherosclerosis, diabetes mellitus, a transient ischemic event, a secondary ischemic event, vascular death with established peripheral arterial disease, cardiovascular disease, cerebrovascular disease, angina pectoris, cardiac arrhythmia, sickle cell crisis, and combinations thereof.

21. The method of claim 17, further comprising administering a second therapeutic agent selected from: a nonsteroidal antiinflamatory drug, a selective factor Xa inhibitor, a direct thrombin inhibitor, a prostaglandin analog, an adenosine diphosphate (ADP) inhibitor, a platelet aggregation inhibitor, an antiplatelet agent, a glycoprotein IIb/IIIa inhibitor or antagonist, an antisickling agent, a hemorrheologic agent, a thrombolytic agent, a thrombolytic enzyme, a thromboxane A2 biosynthesis inhibitors, a thromboxane antagonist, a cyclooxygenase inhibitor, an angiotensin antagonist, an endothelin antagonist, a phosphodiesterase inhibitor, an angiotensin converting enzyme (ACE) inhibitors, a neutral endopeptidase inhibitors, an anticoagulants, a diuretic, a tissue plasminogen activator, a modified tissue plasminogen activator, a biologic response modifier, a statin, a calcium channel blocking agent, an anti-arrhythmic agent, an α-adrenergic agonist, a β-adrenergic antagonist, and combinations thereof.

22. The method of claim 17, further comprising administering a second therapeutic agent selected from: clopridogrel, diclofenac, droxicam, etolodac, fenoprofen, flurbiprofen, indomethacin, isoxicam, ketoprofen, lornoxicam, meloxicam, mefenamate, naproxen, oxaprozin, piroxicam, sulindac, tenoxicam, apixaban, otamixaban, rivaroxaban, eptifibatide, beraprost, prostacyclin, iloprost, treprostinil, ticagrelor, ticlopidine, abciximab, cloricromen, ditazole, indobufen, picotamide, sulfinpyrazone, eptifibatide, tirofiban, cetiedil, alteplase, anistreplase, brinase, drotrecogin alfa, monteplase, reteplase, saruplase, streptokinase, tenecteplase, urokinase, fibrinolysin, ancrod, aspirin, picotamide, ramatroban, seratrodast, aloxiprin, carbasalate calcium, celecoxib, ibuprofen, rofecoxib, candesartan, eprosartan, irbesartan, losartan, olmesartan, telmisartan, valsartan, ambrisentan, atrasentan, bosentan, sitaxentan, tezosentan, cilostazol, dipyridamole, enoximone, milrinone, captopril, enalapril, enaliprilat, spirapril, quinapril, perindopril, ramipril, fosinopril, trandolapril, lisinopril, moexipril, benazapril, candoxatril, ecadotril, unfractionated heparin, ardeparin, bemiparin, certoparin, dalteparin, enoxaparin, fondaparin, fragmin, melagatran, nadroparin, parnaparin, reviparin, tinzaparin, argatroban, dabigatran, melagatran, ximelagatran, defibrotide, ramatroban, antithrombin III, fondaparinux, idraparinux, danaparoid, sulodexide, dermatan sulfate, a hirudin, disulfatohirudin bivalirudin, desirudin, lepirudin, acenocoumarol, dicoumarol, ethyl biscoumacetate, phenprocoumon, clorindione, diphenadione, phenindione, tioclomarol, warfarin, chlorothiazide, hydrochlorothiazide, ethacrynic acid, furosemide, amiloride, chlorothiazide, hydrochlorothiazide, atorvastatin, fluvastatin, lovastatin, pravastatin, rosuvastatin, simvastatin, amlodipine, felodipine, diltiazem, nifedipine, nicardipine, nisoldipine, bepridil, verapamil, dofetilide, ibutilide, metoprolol, propranolol, atenolol, betaxolol, bisoprolol, carvediol, nadolol, nebivolol, timolol, ajmaline, disopyramide, prajmaline, procainamide, quinidine, sparteine, aprindine, lidocaine, mexiletine, tocainide, encainide, flecainide, lorcainide, moricizine, propafenone, acebutolol, pindolol, amiodarone, bretylium, bunaftine, sotalol, adenosine, atropine, digoxin, doxazosin, terazosin, prazosin, and combinations thereof.

* * * * *